US007229795B2

(12) United States Patent
Dartois et al.

(10) Patent No.: US 7,229,795 B2
(45) Date of Patent: Jun. 12, 2007

(54) 2,5-DKG PERMEASES

(75) Inventors: Veronique A. Dartois, San Diego, CA (US); James A. Hoch, La Jolla, CA (US); Fernando Valle, Burlingame, CA (US); Manoj Kumar, Fremont, CA (US)

(73) Assignees: Genencor International, Inc., Palo Alto, CA (US); E.P.I. Liquidation Co., La Jolla, CA (US)

( * ) Notice: Subject to any disclaimer, the term of this patent is extended or adjusted under 35 U.S.C. 154(b) by 294 days.

(21) Appl. No.: 10/787,267

(22) Filed: Feb. 25, 2004

(65) Prior Publication Data
US 2005/0032088 A1 Feb. 10, 2005

Related U.S. Application Data

(62) Division of application No. 09/922,501, filed on Aug. 3, 2001, now Pat. No. 6,720,168.

(60) Provisional application No. 60/421,141, filed on Sep. 29, 2000, provisional application No. 60/325,774, filed on Aug. 4, 2000.

(51) Int. Cl.
C12P 19/00 (2006.01)
C12N 1/20 (2006.01)
(52) U.S. Cl. ............ 435/72; 435/252.3; 435/320.1; 435/183; 536/23.2; 536/23.7
(58) Field of Classification Search ............ 435/183, 435/252.3, 320.1, 72; 536/23.2, 27.2
See application file for complete search history.

(56) References Cited

U.S. PATENT DOCUMENTS

| 4,757,012 A | 7/1988 | Estell et al. ............ 435/172.3 |
| 5,032,514 A | 7/1991 | Anderson et al. ........ 435/138 |
| 5,047,340 A | 9/1991 | Dickson et al. ............ 435/161 |
| 5,783,431 A | 7/1998 | Peterson et al. ......... 435/172.3 |
| 5,912,161 A | 6/1999 | Lazarus et al. .......... 435/252.3 |
| 5,958,672 A | 9/1999 | Short ........................ 435/4 |
| 5,989,891 A | 11/1999 | Liaw et al. ............... 435/244 |
| 6,022,719 A | 2/2000 | Hubbs ...................... 435/138 |
| 6,368,793 B1* | 4/2002 | Hoch et al. ................. 435/6 |
| 6,833,447 B1* | 12/2004 | Goldman et al. ......... 536/23.1 |

FOREIGN PATENT DOCUMENTS

| DE | 195 23 279 A | 1/1997 |
| EP | 0 839 909 A | 5/1998 |
| FR | 2 736 652 A | 1/1997 |
| WO | WO 95/10613 | 4/1995 |
| WO | WO 97/25432 A | 7/1997 |
| WO | WO 98/18936 A | 5/1998 |
| WO | WO 02/12528 A | 2/2002 |
| WO | WO 00/22170 | 4/2002 |

OTHER PUBLICATIONS

Mahairas, G.G., et al. (1999) Proc. Natl. Acad. Sci., USA 96, 9739-9744.*
* Bausch et al., Sequence analysis of the Gntill (subsidiary) system for gluconate metabolism reveals a novel pathway for L-idonic acid catabolism in *Escherichia coil*, *J. of Bacteriology*, V. 180(14), Jul. 1998, pp. 3704-3710.
* Boudrant, J. "Miicrobial processes for ascorbic acid biosynthesis: a review," *Enzyme and Microbial Technology*, V. 12,(5), May 1, 1990, pp. 322-329.
* Chotani, et al., The commercial productin of chemicals using pathway engineering, *Biochimica et Biophysica acta*, V. 1543 (2), Dec. 2000, pp. 434-455.
*Eroshkin et al., "Algorithm and cmputer program Pro_Anal for analysis of relationship between structure and activity in a family of proteins or peptides," *Comput. Appl. Biosci.*, vol. 9, pp. 491-497, 1993.
*Hamilton et al., "New Method for Generating Deletions and Gene Replacements," *J. Bacteriol.*, vol. 171, No. 9, pp. 4617-4622, 1989.
*Higgens, D., "Clustal V: Multiple Alignment of DNA and Protein Sequences," *Methods Mol. Biol.*, vol. 25, pp. 307-318, 1994.
*Hamood et al., Pseudomonas aeruginosa PtxR (ptxR) and PtxS) genes, complete cds and ketogluconate utilization operon gene, complete sequence, Database accession No. AF012100 XP002204795.
*Huse et al., "Geneation of a Large combinatorial Library of the Immunoglobulin Repertoire in Phage Lambda," *Science*, vol. 246, pp. 1275-1281, 1989.
*Irnaten et al., "Prediction of epitopes and production of monoclonal antibodies against gastric H,K-ATPase," *Protein, Eng.*, vol. 11 No. 10, pp. 949-955, 1998.
*Izu, et al., "Characterization of the gnlT gene encoding aq high-affinity gluconate permease in *Escherichia coli*" *Gene* 199 (1997) pp. 203-210.
*Klemm, et al., "The gntP Gene of *Escherichia coli*Involved in Gluconate Uptake," *J. of Bacteriology*, Jan. 1996, p. 61-67, V178 (1).
*Kramer, R., << Genetic and physiological approaches for the production of amino acids <<, J. of Biotechnology, Elsevier Science Publishers, Amsterdam, NL, V.45(1), Feb. 12, 1996.pp. 1-21.

(Continued)

Primary Examiner—Tekchand Saidha
(74) Attorney, Agent, or Firm—Lynn Marcus-Wyner

(57) ABSTRACT

The invention provides isolated nucleic acid molecules encoding polypeptides having 2,5-DKG permease activity, and oligonucleotides therefrom. The isolated nucleic acid molecules can be expressed in appropriate bacterial cells to enhance the production of 2-KLG, which can subsequently be converted to ascorbic acid. Further provided are isolated polypeptides having 2,5-DKG permease activity, immunogenic peptides therefrom, and antibodies specific therefor. The invention also provides methods of identifying novel 2,5-DKG permeases.

28 Claims, 4 Drawing Sheets

OTHER PUBLICATIONS

*Pao et al., << Major facilitator superfamily, >> Microbiology and Molecular Biology Reviews, V.62(1), Mar. 1998, pp. 1-34.

*Lerner et al., "Low copy number plasmids for regulated low-level expression of cloned genes in Escherichia coli with blue/white insert screening capability," Nucleic Acids Res., vol. 18, No. 15, pp. 4631, 1990.

*Peekhaus, et al., Characterization of a novel transporter family that includes multiple Escherichia coli gluconate transporters and their homologues, Fems Microbiology Letters, V. 147(2), 1997, pp. 233-238.

*Saito, et al. "Direct fermentation of 2-Keto-L-gulonic acid in recombinant Gluconbacter oxydans," Biotechnology and Bioengineering, V. 58(2-3), Apr. 20, 1998, pp. 309-315.

*Savoie et al., "Use of BONSAI decision trees for the identification of potential MHC Class I peptide epitope motifs," Pac Symp. Biocomput., 1999:184-489, 1999.

*Streicher et al., "Transduction of the Nitrogen-fixation genes in Klebsiella pneumoniae," Proc. Natl. Acad. Sci., vol. 68, pp. 1174-1177, 1971.

*Swanson et al., "Characterization of the 2-ketogluconate utilization operon in Pseudomonas aeruginosa PA01," molecular microbiology, 37(3):561-575 (2000).

*Ward et al., "Binding activities of a repertire of single immunoglobulin variable domains secreted from Escherichia coli" Nature, vol. 341, pp. 544-546, 1989.

*Winter and Harris, "Humanized antibodies," Immunol. Today, vol. 14, pp. 243-246, 1993.

*Yew, et al., << Utilization of L-ascorbate by Escheriuchia coli K-12 : Assignments of functions to products of the yjf-sga and yia-sgb operons, >> J. of Bacteriology, V. 184 (1), Jan. 2002, pp. 302-306.

* cited by examiner

```
yiaX2   MNITSNSTTKD--IPRQRWLRIIPPILITCIISYMDRVNIAFAMPGGMDA
prmA    MQ---------KSQPGTRWFRIIVPILIACIMSFMDRVNISFALPGGMEQ
PE6     MNTASVSVTQSQAIPKLRWLRIVPPILITCIISYMDRVNIAFAMPGGMDD
PK1     MNSST-------N-ATKRWWYIMPIVFITYSLAYLDRANFSFASAAGITE
prmB    MNTSR-------KLPVKRWWYLMPVIFITYSLAYLDRANYGFAAASGIEA
PE1     MNSST-------N-ATKRWWYIMPIVFITYSLAYLDRANFSFASAAGITE
        *.           .  **  .. ..*.  ....** * .** ..*.

yiaX2   DLGISATMAGLAGGIFFIGYLFLQVPGGKIAVHGSGKKFIGWSLVAWAVI
prmA    DLLMSSQMAGVVSGIFFIGYLFLQVPGGHIAVRGSGKRFIAWSLVAWAVV
PE6     ELGITASMAGLAGGIFFIGYLFLQVPGGKLAVYGNGKKFIGWSLLAWAVI
PK1     DLGITKGISSLLGALFFLGYFFFQIPGAIYAERRSVRKLIFICLILWGAC
prmB    DLGISRGTSSLIGALFFLGYFIFQVPGAIYAVKRSVRKLVFTSLLLWGFC
PE1     DLGITKGISSLLGALFFLGYFFFQIPGAIYAERRSVRKLIFICLILWGAC
        .* ..      ... ...**.**...*.**.  *   ....    *. *.

yiaX2   SVLT-GLITNQYQLLALRFLLGVAEGGMLPVVLTMISNWFPDAERGRANA
prmA    SVAT-GFVTHQYQLLILRFALGVSEGGMLPVVLTMVSNWFPEKELGRANA
PE6     SVLT-GLVTNQYQLLFLRFALGRFSGMLRWVLTMISNWFPDKERGRANA
PK1     ASLDRDGAQYSRAGRAIRFILGVVEAAVMPAMLIYISNWFTKSERSRANT
prmB    AA-ATGLISNIPALMVIRFVLGVVEAAVMPAMLIYISNWFTRQERSRANT
PE1     ASLDRDGAQYSSAGWRSVLFSAVVEAAVMPAMLIYISNWFTKSERSRANT
         .   .         . .   .... .* .****   * .***.

yiaX2   IVIMFVPIAGIITAPLSGWIITVLDWRWLFIIEGLLSLVVLVLWAYTIYD
prmA    FVMMFAPLGGMITAPVSGWIIALLDWRWLFIIEGLLSVVVLAVWWLMVSD
PE6     IVIMFVPIAGILTAPLSGWIITAWDWRMLFLVEGALSLVVMLWYFTISN
PK1     FLILGNPVTVLWMSVVSGYLIQAFGWREMFIIEGVPAVIWAFCWWVLVKD
prmB    FLVLGNPVTVLWMSIVSGYLINAFGWREMFIFEGVPALIWAIFWWFIVRD
PE1     FLILGNPVTVLWMSVVSGYLIQSFGWREMFIIEGVPAVLWAFCWWVLVKV
        .... *.  .  .**.*    .** .* **  ...      *    .

yiaX2   RPQEARWISEAEKRYLVETLAAEQKAIAG-TEVKNASLSAVLSDKTMWQL
prmA    RPEDARWLPAAEREYLLREMARDKAERSKLPPISHAPLQEVFHNPGLMKL
PE6     RPQEAKRISQAEKDYLIKTLHDEQLLIKG-KTVRNASLRRVLGDKIMWK-
PK1     KPSQVNWLAESEKAALQEQLEREQQGIKPVRNYGEA-----FRSRNVVLL
prmB    KPEQVSWLTETEKQQLASAMAEEQQAIPPMRNVPQA-----LRSRNVVVL
PE1     KPSQVNWLSENEKAALQAQLESEQQGIKAVRNYGEA-----FRSRNVILL
        .*.  ..     *.  *.       . ..              .*  . .
```

FIG. 1A

```
yiaX2   IALNFFYQTGIYGYTLWLPTILKELTHS-SMGQVGMLAILPYVGAIAGMF
prmA    VILNFFYQTGDYGYTLWLPTIIKNLTGA-SIGNVGLLTVLPFIATLSGIY
PE6     ----FFYQTGIYGYTLWLPTILKGLTNG-NMEQVGMLAILPYIGAIFGML
PK1     CMQYFAWSIGVYGFVLWLPSIIRSGGENMGMVEVGWLSSVPYLAATIAMI
prmB    CLLHALWSIGVYGFMMWMPSILRSAA-SMDIVRVGWLAAVPYLAAIITML
PE1     CMQYFAWSIGVYGFVLWLPSIIRSGGVNMGMVEVGWLSSVPYLAATIAMI
         * **. .*.*.*..     . ** *. ..*....    .

yiaX2   LFSSLSDRTGKRKLFV-CLPLIGFALCMFLSVALKNQIWLSYAALVGCGF
prmA    VVSYLSDKTGKRRQWV-MISLFCFAACLLASVLLREFVLAAYLALVACGF
PE6     IISTLSDRTGKRKVFV-ALPLACFAICMALSVLLKDHIWWSYAALVGCGV
PK1     VVSWASDKMQNRKLFVWPLLLIAVFAFIGSWAVGANLSWVSYTLLVIAGA
prmB    VISWLSDKTGLRRLFIWPLLLIASVTFFGSWLLGSYSFWFSYGLLVLAAA
PE1     VVSWASDKMQNRKLFVWPLLLIGGLAFIGSWAVGANHFWASYTLLVIANA
         . * **. *. . .*                 .* ** yiaX2   FLQSAAGVFWTIPARLFSAEMAGGARGVINALGNLGGFCGPYAVGVLITL
prmA    FLKAATSPFWSIPGRIAPPEAAGSARGVINGLGNLGGFCGPWLVGLMIYL
PE6     FTQAAAGVFWTIPPKLFNAEMAGGARGVINALGNLGGFCGPYMVGVLITL
PK1     AMYAPYGPFFAIIPEMLPRNVAGGAMALINSMGALGSFFGSWFVGYLNGT
prmB    CMYAPYGPFFALIPELLPKNVAGISIGLINCCGALGAFAGAWLVGYLNGL
PE1     AMYAPYGPFFAIIPEMLPRNVAGGAMALINSMGALGSFFGSWFVGYLNGT
         .. *  ..  .  ** . ..** * **.* *. ** .

yiaX2   YSKDAGVYC-LAISLALAALMALLLPAKCDAGAAPVK--TINPHKRTA-
prmA    YGQNAAVVT-LAGSLIIAGIIAALLPTQCDLRPAEARQQNFTPRIHDAK
PE6     FSKDVGVYS-LAVSLASASVLALMLPNRCDQKAGA-----------E-
PK1     TGSPSASYIFMGVALFVSVWLTLIVKPA---NNQKLP---LGAR---HA
prmB    TGGPGASYTFMAIALLVSVGLVFFLKVP---SGNLVTRRLLKGD---AK
PE1     TGSPSASYIFMGVALFASVWLTLIVKPA---NNQKLP---IGAR---HA
         .  .  .. .*  .  .
```

*FIG. 1B*

SEQUENCE LISTING

```
<160> NUMBER OF SEQ ID NOS: 22

<210> SEQ ID NO 1
<211> LENGTH: 1500
<212> TYPE: DNA
<213> ORGANISM: Unknown
<220> FEATURE:
<223> OTHER INFORMATION: environmental source
```

```
<220> FEATURE:
<221> NAME/KEY: CDS
<222> LOCATION: (94)...(1374)

<400> SEQUENCE: 1
ggcgaatagc ccggccggcg tcataataac ggccttctct gtaccctaca tacggcggcg      60
gcgtcatgaa cctcaactt agtaggcaag cct atg aac agc tct acc aat gca       114
                                    Met Asn Ser Ser Thr Asn Ala
                                     1               5 acg aaa cgc tgg tgg tac atc atg cct atc gtg ttt atc acg tat agc      162
Thr Lys Arg Trp Trp Tyr Ile Met Pro Ile Val Phe Ile Thr Tyr Ser
         10                  15                  20 ctg gcg tat ctc gac cgc gca aac ttc agc ttt gct tcg gca gcg ggc      210
Leu Ala Tyr Leu Asp Arg Ala Asn Phe Ser Phe Ala Ser Ala Ala Gly
     25                  30                  35 att acg gaa gat tta ggc att acc aaa ggc atc tcg tcg ctt ctt ggc      258
Ile Thr Glu Asp Leu Gly Ile Thr Lys Gly Ile Ser Ser Leu Leu Gly
 40                  45                  50                  55 gca ctt ttc ttc ctc ggc tat ttc ttc ttc cag atc ccg ggg gcg att      306
Ala Leu Phe Phe Leu Gly Tyr Phe Phe Phe Gln Ile Pro Gly Ala Ile
                 60                  65                  70 tac gcg gaa cgc cgt agc gta cgg aag ctg att ttc atc tgt ctg atc      354
Tyr Ala Glu Arg Arg Ser Val Arg Lys Leu Ile Phe Ile Cys Leu Ile
             75                  80                  85 ctg tgg ggc gcc tgc gcc tcg ctt gac cgg gat ggt gca caa tat tcc      402
Leu Trp Gly Ala Cys Ala Ser Leu Asp Arg Asp Gly Ala Gln Tyr Ser
         90                  95                 100 agc gct ggc tgg cga tcc gtt tta ttc tcg gct gtc gtg gaa gcg gcg      450
Ser Ala Gly Trp Arg Ser Val Leu Phe Ser Ala Val Val Glu Ala Ala
     105                 110                 115 gtc atg ccg gcg atg ctg att tac atc agt aac tgg ttt acc aaa tca      498
Val Met Pro Ala Met Leu Ile Tyr Ile Ser Asn Trp Phe Thr Lys Ser
120                 125                 130                 135 gaa cgt tca cgc gcc aac acc ttc tta atc ctc ggc aac ccg gtc acg      546
Glu Arg Ser Arg Ala Asn Thr Phe Leu Ile Leu Gly Asn Pro Val Thr
                 140                 145                 150 gta ctg tgg atg tcg gtg gtc tcc ggc tac ctg att cag tcc ttc ggc      594
Val Leu Trp Met Ser Val Val Ser Gly Tyr Leu Ile Gln Ser Phe Gly
             155                 160                 165 tgg cgt gaa atg ttt att att gaa ggc gtt ccg gcc gtc ctc tgg gcc      642
Trp Arg Glu Met Phe Ile Ile Glu Gly Val Pro Ala Val Leu Trp Ala
         170                 175                 180 ttc tgc tgg tgg gtg ctg gtc aaa gtt aaa ccg tcg cag gtg aac tgg      690
Phe Cys Trp Trp Val Leu Val Lys Val Lys Pro Ser Gln Val Asn Trp
     185                 190                 195 ttg tcg gaa aac gag aaa gcc gcg ctg cag gcg cag ctg gag agc gag      738
Leu Ser Glu Asn Glu Lys Ala Ala Leu Gln Ala Gln Leu Glu Ser Glu
200                 205                 210                 215 cag cag ggt att aaa gcc gtg cgt aac tac ggc gaa gcc ttc cgc tca      786
Gln Gln Gly Ile Lys Ala Val Arg Asn Tyr Gly Glu Ala Phe Arg Ser
                 220                 225                 230 cgc aac gtc att cta ctg tgc atg cag tat ttt gcc tgg agt atc ggc      834
Arg Asn Val Ile Leu Leu Cys Met Gln Tyr Phe Ala Trp Ser Ile Gly
             235                 240                 245 gtg tac ggt ttt gtg ctg tgg ttg ccg tca att att cgc agc ggc ggc      882
Val Tyr Gly Phe Val Leu Trp Leu Pro Ser Ile Ile Arg Ser Gly Gly
         250                 255                 260 gtc aat atg ggg atg gtg gaa gtc ggc tgg ctc tct tcg gtg cct tat      930
Val Asn Met Gly Met Val Glu Val Gly Trp Leu Ser Ser Val Pro Tyr
     265                 270                 275
```

```
ctg gcc gcg act att gcg atg atc gtc gtc tcc tgg gct tcc gat aaa      978
Leu Ala Ala Thr Ile Ala Met Ile Val Val Ser Trp Ala Ser Asp Lys
280                 285                 290                 295 atg cag aac cgt aaa ctg ttc gtc tgg ccg ctg ctg att ggc gga          1026
Met Gln Asn Arg Lys Leu Phe Val Trp Pro Leu Leu Ile Gly Gly
                300                 305                 310 ctg gct ttt att ggc tca tgg gcc gtc ggc gct aac cat ttc tgg gcc      1074
Leu Ala Phe Ile Gly Ser Trp Ala Val Gly Ala Asn His Phe Trp Ala
            315                 320                 325 tct tat acc ctg ctg gtg att gcc aat gcg gca atg tac gcc cct tac      1122
Ser Tyr Thr Leu Leu Val Ile Ala Asn Ala Ala Met Tyr Ala Pro Tyr
        330                 335                 340 ggt ccg ttt ttc gcc atc att ccg gaa atg ctg ccg cgt aac gtc gcc      1170
Gly Pro Phe Phe Ala Ile Ile Pro Glu Met Leu Pro Arg Asn Val Ala
    345                 350                 355 ggt ggc gca atg gcg ctc atc aac agc atg ggg gcc tta ggt tca ttc      1218
Gly Gly Ala Met Ala Leu Ile Asn Ser Met Gly Ala Leu Gly Ser Phe
360                 365                 370                 375 ttt ggt tcg tgg ttc gtg ggc tac ctg aac ggc acc acc ggc agt cca      1266
Phe Gly Ser Trp Phe Val Gly Tyr Leu Asn Gly Thr Thr Gly Ser Pro
                380                 385                 390 tca gcc tca tac att ttc atg gga gtg gcg ctt ttc gcc tcg gta tgg      1314
Ser Ala Ser Tyr Ile Phe Met Gly Val Ala Leu Phe Ala Ser Val Trp
            395                 400                 405 ctt act tta att gtt aag cct gct aac aat caa aag ctc ccc atc ggc      1362
Leu Thr Leu Ile Val Lys Pro Ala Asn Asn Gln Lys Leu Pro Ile Gly
        410                 415                 420 gct cgt cac gcc tgacctttac tacttacgga gatcacgcct tgggtacgtt          1414
Ala Arg His Ala
        425 gcaggacaaa ccgataggca ccgcaaaggc tggggccatc gagcagcgcg taaacagtca    1474 gctggttgct gtcgctgtgc ggcgtc                                         1500

<210> SEQ ID NO 2
<211> LENGTH: 427
<212> TYPE: PRT
<213> ORGANISM: Unknown
<220> FEATURE:
<223> OTHER INFORMATION: environmental source

<400> SEQUENCE: 2

Met Asn Ser Ser Thr Asn Ala Thr Lys Arg Trp Trp Tyr Ile Met Pro
1               5                   10                  15

Ile Val Phe Ile Thr Tyr Ser Leu Ala Tyr Leu Asp Arg Ala Asn Phe
            20                  25                  30

Ser Phe Ala Ser Ala Ala Gly Ile Thr Glu Asp Leu Gly Ile Thr Lys
        35                  40                  45

Gly Ile Ser Ser Leu Leu Gly Ala Leu Phe Phe Leu Gly Tyr Phe Phe
    50                  55                  60

Phe Gln Ile Pro Gly Ala Ile Tyr Ala Glu Arg Arg Ser Val Arg Lys
65                  70                  75                  80

Leu Ile Phe Ile Cys Leu Ile Leu Trp Gly Ala Cys Ala Ser Leu Asp
                85                  90                  95

Arg Asp Gly Ala Gln Tyr Ser Ser Ala Gly Trp Arg Ser Val Leu Phe
            100                 105                 110

Ser Ala Val Val Glu Ala Ala Val Met Pro Ala Met Leu Ile Tyr Ile
        115                 120                 125
```

```
Ser Asn Trp Phe Thr Lys Ser Glu Arg Ser Arg Ala Asn Thr Phe Leu
        130                 135                 140

Ile Leu Gly Asn Pro Val Thr Val Leu Trp Met Ser Val Val Ser Gly
145                 150                 155                 160

Tyr Leu Ile Gln Ser Phe Gly Trp Arg Glu Met Phe Ile Ile Glu Gly
                165                 170                 175

Val Pro Ala Val Leu Trp Ala Phe Cys Trp Trp Val Leu Val Lys Val
            180                 185                 190

Lys Pro Ser Gln Val Asn Trp Leu Ser Glu Asn Glu Lys Ala Ala Leu
        195                 200                 205

Gln Ala Gln Leu Glu Ser Glu Gln Gln Gly Ile Lys Ala Val Arg Asn
    210                 215                 220

Tyr Gly Glu Ala Phe Arg Ser Arg Asn Val Ile Leu Leu Cys Met Gln
225                 230                 235                 240

Tyr Phe Ala Trp Ser Ile Gly Val Tyr Gly Phe Val Leu Trp Leu Pro
                245                 250                 255

Ser Ile Ile Arg Ser Gly Gly Val Asn Met Gly Met Val Glu Val Gly
                260                 265                 270

Trp Leu Ser Ser Val Pro Tyr Leu Ala Ala Thr Ile Ala Met Ile Val
        275                 280                 285

Val Ser Trp Ala Ser Asp Lys Met Gln Asn Arg Lys Leu Phe Val Trp
290                 295                 300

Pro Leu Leu Ile Gly Gly Leu Ala Phe Ile Gly Ser Trp Ala Val
305                 310                 315                 320

Gly Ala Asn His Phe Trp Ala Ser Tyr Thr Leu Leu Val Ile Ala Asn
                325                 330                 335

Ala Ala Met Tyr Ala Pro Tyr Gly Pro Phe Phe Ala Ile Ile Pro Glu
            340                 345                 350

Met Leu Pro Arg Asn Val Ala Gly Gly Ala Met Ala Leu Ile Asn Ser
        355                 360                 365

Met Gly Ala Leu Gly Ser Phe Phe Gly Ser Trp Phe Val Gly Tyr Leu
    370                 375                 380

Asn Gly Thr Thr Gly Ser Pro Ser Ala Ser Tyr Ile Phe Met Gly Val
385                 390                 395                 400

Ala Leu Phe Ala Ser Val Trp Leu Thr Leu Ile Val Lys Pro Ala Asn
                405                 410                 415

Asn Gln Lys Leu Pro Ile Gly Ala Arg His Ala
            420                 425
```

<210> SEQ ID NO 3
<211> LENGTH: 1775
<212> TYPE: DNA
<213> ORGANISM: Unknown
<220> FEATURE:
<223> OTHER INFORMATION: environmental source
<220> FEATURE:
<221> NAME/KEY: CDS
<222> LOCATION: (214)...(1491)

<400> SEQUENCE: 3

```
ggcaatttgc ggtgtttttt ccgcaggacg ttcatcgtcc ggcctgtatt catcaacggc     60
cctgcgctat tcgcaaagtg gtggtgaaaa taccgctgcg ttatttaacg cccaataagc    120
aacaccgagt ttataaccct gaacgacacg gctgcgggcc tgtgtagacg cccctacgcc    180
ttaacaccac taaatgactc tacaggtgta tat atg aat aca gcc tct gtt tct    234
                                    Met Asn Thr Ala Ser Val Ser
                                    1               5
```

-continued

| | |
|---|---|
| gtc acc caa agc cag gcg atc ccc aaa tta cgc tgg ttg aga ata gtg<br>Val Thr Gln Ser Gln Ala Ile Pro Lys Leu Arg Trp Leu Arg Ile Val<br>      10                       15                       20 | 282 |
| ccg cct att ctt att acc tgc att att tcc tat atg gac cgg gtg aac<br>Pro Pro Ile Leu Ile Thr Cys Ile Ile Ser Tyr Met Asp Arg Val Asn<br>     25                     30                   35 | 330 |
| atc gcc ttc gcc atg ccc ggc ggc atg gac gat gaa ctg ggc atc acc<br>Ile Ala Phe Ala Met Pro Gly Gly Met Asp Asp Glu Leu Gly Ile Thr<br>40                     45                   50                   55 | 378 |
| gcc tcg atg gcc ggg ttg gcc ggc ggt att ttc ttt atc ggt tat ctg<br>Ala Ser Met Ala Gly Leu Ala Gly Gly Ile Phe Phe Ile Gly Tyr Leu<br>             60                     65                   70 | 426 |
| ttc ttg cag gta ccc ggc ggc aag ctg gcg gtg tac ggc aac ggc aag<br>Phe Leu Gln Val Pro Gly Gly Lys Leu Ala Val Tyr Gly Asn Gly Lys<br>               75                     80                   85 | 474 |
| aaa ttc atc ggt tgg tcg ttg ttg gcc tgg gcg gtg att tcc gtg ctg<br>Lys Phe Ile Gly Trp Ser Leu Leu Ala Trp Ala Val Ile Ser Val Leu<br>     90                     95                  100 | 522 |
| acc ggg ctg gtc acg aat cag tat caa ttg ctg ttc ctg cgc ttc gcc<br>Thr Gly Leu Val Thr Asn Gln Tyr Gln Leu Leu Phe Leu Arg Phe Ala<br>105                   110                 115 | 570 |
| ctc ggc cgt ttc cga agc ggc atg ctg cgg tgg gtg ctg acc atg atc<br>Leu Gly Arg Phe Arg Ser Gly Met Leu Arg Trp Val Leu Thr Met Ile<br>120                 125               130              135 | 618 |
| agc aac tgg ttc ccg gac aag gaa cgc ggg cgc gcc aac gcc atc gtc<br>Ser Asn Trp Phe Pro Asp Lys Glu Arg Gly Arg Ala Asn Ala Ile Val<br>             140                 145               150 | 666 |
| atc atg ttc gtg ccg atc gcc ggc atc ctt acc gca ccg ctg tcc ggc<br>Ile Met Phe Val Pro Ile Ala Gly Ile Leu Thr Ala Pro Leu Ser Gly<br>               155                 160               165 | 714 |
| tgg atc atc acc gcc tgg gac tgg cgc atg ctg ttc ctg gtc gag ggc<br>Trp Ile Ile Thr Ala Trp Asp Trp Arg Met Leu Phe Leu Val Glu Gly<br>             170                 175               180 | 762 |
| gcg ctg tcg ctg gtc gtg atg gtg ctg tgg tat ttc acc atc agc aac<br>Ala Leu Ser Leu Val Val Met Val Leu Trp Tyr Phe Thr Ile Ser Asn<br>185                   190                 195 | 810 |
| cgt cca caa gag gcc aaa agg att tcg cag gcg gaa aaa gat tat ctg<br>Arg Pro Gln Glu Ala Lys Arg Ile Ser Gln Ala Glu Lys Asp Tyr Leu<br>200                 205               210              215 | 858 |
| atc aaa acg ctg cac gac gaa cag ttg ctg atc aaa ggc aaa acg gtg<br>Ile Lys Thr Leu His Asp Glu Gln Leu Leu Ile Lys Gly Lys Thr Val<br>             220                 225               230 | 906 |
| cgc aac gcc tcg ctg cgt cgg gtg ctg ggc gac aaa atc atg tgg aag<br>Arg Asn Ala Ser Leu Arg Arg Val Leu Gly Asp Lys Ile Met Trp Lys<br>               235                 240               245 | 954 |
| ttc ttc tac cag acc ggg ata tac ggc tac acc ctg tgg ctg ccg acc<br>Phe Phe Tyr Gln Thr Gly Ile Tyr Gly Tyr Thr Leu Trp Leu Pro Thr<br>             250                 255               260 | 1002 |
| att ctc aag ggg ctc acc aac ggc aat atg gag cag gtc ggg atg ctg<br>Ile Leu Lys Gly Leu Thr Asn Gly Asn Met Glu Gln Val Gly Met Leu<br>265                   270                 275 | 1050 |
| gct atc ctg ccc tat atc ggc gcc atc ttc ggc atg ctg atc att tcc<br>Ala Ile Leu Pro Tyr Ile Gly Ala Ile Phe Gly Met Leu Ile Ile Ser<br>280                   285               290              295 | 1098 |
| acc ctc tcc gat cgc acc ggc aag cgc aaa gtg ttc gtc gca ctg ccg<br>Thr Leu Ser Asp Arg Thr Gly Lys Arg Lys Val Phe Val Ala Leu Pro<br>             300                 305               310 | 1146 |
| ctg gcc tgc ttt gcc atc tgc atg gcg ctg tcg gtg ctg ctg aag gat<br>Leu Ala Cys Phe Ala Ile Cys Met Ala Leu Ser Val Leu Leu Lys Asp | 1194 |

-continued

```
              315                 320                 325
cac atc tgg tgg tcg tac gcg gcg ctg gtg ggc tgt ggc gtc ttt acc      1242
His Ile Trp Trp Ser Tyr Ala Ala Leu Val Gly Cys Gly Val Phe Thr
            330                 335                 340 cag gcc gcc gcc ggg gtg ttc tgg acc att ccg ccc aag ctg ttt aac      1290
Gln Ala Ala Ala Gly Val Phe Trp Thr Ile Pro Pro Lys Leu Phe Asn
        345                 350                 355 gcc gaa atg gcc ggc ggc gcg cgc ggc gtg atc aat gca ctg ggc aac      1338
Ala Glu Met Ala Gly Gly Ala Arg Gly Val Ile Asn Ala Leu Gly Asn
360                 365                 370                 375 ctc ggc ggt ttc tgc ggc ccc tat atg gtc ggc gtg ttg atc acc ttg      1386
Leu Gly Gly Phe Cys Gly Pro Tyr Met Val Gly Val Leu Ile Thr Leu
                380                 385                 390 ttc agc aaa gac gtc ggc gtt tac agc ctc gcg gtg tcg ctg gcc tcc      1434
Phe Ser Lys Asp Val Gly Val Tyr Ser Leu Ala Val Ser Leu Ala Ser
            395                 400                 405 gcc tcg gtg ctg gcg ttg atg ctg ccg aac aga tgc gac caa aaa gcg      1482
Ala Ser Val Leu Ala Leu Met Leu Pro Asn Arg Cys Asp Gln Lys Ala
        410                 415                 420 ggg gcc gaa taatggacta ttgctgggg ctggactgcg gcggcacctt              1531
Gly Ala Glu
    425 tatcaaagcc ggcctgtatg accggaatgg cgcagaactg gcatagccc gccgtacgct     1591 ggacattgtc gcgccgcaac ccggctgggc ggaacgtgac atgcccgcgc tgtggcagac    1651 cgccgccgag gtgatccgcg aattgctggc ccgcaacgac attgccgacg ctgatattca    1711 ggccatcggc atctcggcgc agggtaaagg cgcgtttttg ttagacgagc aaggccaacc    1771 gttg                                                                 1775
```

<210> SEQ ID NO 4
<211> LENGTH: 426
<212> TYPE: PRT
<213> ORGANISM: Unknown
<220> FEATURE:
<223> OTHER INFORMATION: environmental source

<400> SEQUENCE: 4

```
Met Asn Thr Ala Ser Val Ser Val Thr Gln Ser Gln Ala Ile Pro Lys
1               5                   10                  15

Leu Arg Trp Leu Arg Ile Val Pro Pro Ile Leu Ile Thr Cys Ile Ile
            20                  25                  30

Ser Tyr Met Asp Arg Val Asn Ile Ala Phe Ala Met Pro Gly Gly Met
        35                  40                  45

Asp Asp Glu Leu Gly Ile Thr Ala Ser Met Ala Gly Leu Ala Gly Gly
    50                  55                  60

Ile Phe Phe Ile Gly Tyr Leu Phe Leu Gln Val Pro Gly Gly Lys Leu
65              70                  75                  80

Ala Val Tyr Gly Asn Gly Lys Lys Phe Ile Gly Trp Ser Leu Leu Ala
            85                  90                  95

Trp Ala Val Ile Ser Val Leu Thr Gly Leu Val Thr Asn Gln Tyr Gln
        100                 105                 110

Leu Leu Phe Leu Arg Phe Ala Leu Gly Arg Phe Arg Ser Gly Met Leu
    115                 120                 125

Arg Trp Val Leu Thr Met Ile Ser Asn Trp Phe Pro Asp Lys Glu Arg
130                 135                 140

Gly Arg Ala Asn Ala Ile Val Ile Met Phe Val Pro Ile Ala Gly Ile
```

-continued

```
             145                 150                 155                 160
        Leu Thr Ala Pro Leu Ser Gly Trp Ile Ile Thr Ala Trp Asp Trp Arg
                        165                 170                 175
        Met Leu Phe Leu Val Glu Gly Ala Leu Ser Leu Val Val Met Val Leu
                        180                 185                 190
        Trp Tyr Phe Thr Ile Ser Asn Arg Pro Gln Glu Ala Lys Arg Ile Ser
                        195                 200                 205
        Gln Ala Glu Lys Asp Tyr Leu Ile Lys Thr Leu His Asp Glu Gln Leu
                210                 215                 220
        Leu Ile Lys Gly Lys Thr Val Arg Asn Ala Ser Leu Arg Arg Val Leu
        225                 230                 235                 240
        Gly Asp Lys Ile Met Trp Lys Phe Phe Tyr Gln Thr Gly Ile Tyr Gly
                        245                 250                 255
        Tyr Thr Leu Trp Leu Pro Thr Ile Leu Lys Gly Leu Thr Asn Gly Asn
                        260                 265                 270
        Met Glu Gln Val Gly Met Leu Ala Ile Leu Pro Tyr Ile Gly Ala Ile
                        275                 280                 285
        Phe Gly Met Leu Ile Ile Ser Thr Leu Ser Asp Arg Thr Gly Lys Arg
                        290                 295                 300
        Lys Val Phe Val Ala Leu Pro Leu Ala Cys Phe Ala Ile Cys Met Ala
        305                 310                 315                 320
        Leu Ser Val Leu Leu Lys Asp His Ile Trp Trp Ser Tyr Ala Ala Leu
                        325                 330                 335
        Val Gly Cys Gly Val Phe Thr Gln Ala Ala Gly Val Phe Trp Thr
                        340                 345                 350
        Ile Pro Pro Lys Leu Phe Asn Ala Glu Met Ala Gly Ala Arg Gly
                        355                 360                 365
        Val Ile Asn Ala Leu Gly Asn Leu Gly Gly Phe Cys Gly Pro Tyr Met
                        370                 375                 380
        Val Gly Val Leu Ile Thr Leu Phe Ser Lys Asp Val Gly Val Tyr Ser
        385                 390                 395                 400
        Leu Ala Val Ser Leu Ala Ser Ala Ser Val Leu Ala Leu Met Leu Pro
                        405                 410                 415
        Asn Arg Cys Asp Gln Lys Ala Gly Ala Glu
                        420                 425

<210> SEQ ID NO 5
<211> LENGTH: 1478
<212> TYPE: DNA
<213> ORGANISM: Klebsiella oxytoca
<220> FEATURE:
<221> NAME/KEY: CDS
<222> LOCATION: (73)...(1353)

<400> SEQUENCE: 5
ttgcccgccg ccgctgctca gaccatcgat cttttctatg atgagcgtca cctcactcac       60
agaggcaaac ct atg aat agt tca acg aat gca aca aaa cgc tgg tgg tac      111
           Met Asn Ser Ser Thr Asn Ala Thr Lys Arg Trp Trp Tyr
             1               5                  10 atc atg cct atc gtg ttt atc acg tat agc ctg gcg tac ctc gac cgc      159
Ile Met Pro Ile Val Phe Ile Thr Tyr Ser Leu Ala Tyr Leu Asp Arg
         15                  20                  25 gct aac ttc agc ttc gct tcg gcg gcc gga att act gaa gac ctg ggg      207
Ala Asn Phe Ser Phe Ala Ser Ala Ala Gly Ile Thr Glu Asp Leu Gly
     30                  35                  40                  45 atc acc aaa ggt atc tcc tcc ctt ctg ggg gcg ctg ttc ttc ctc ggc      255
```

-continued

```
                Ile Thr Lys Gly Ile Ser Ser Leu Leu Gly Ala Leu Phe Phe Leu Gly
                             50                  55                  60 tac ttc ttc ttt cag atc ccc ggc gcg att tat gcc gaa cgc cgc agc        303
Tyr Phe Phe Phe Gln Ile Pro Gly Ala Ile Tyr Ala Glu Arg Arg Ser
                 65                  70                  75 gta cgt aaa ctc att ttc atc tgc ctg atc ctg tgg ggt gcc tgc gcc        351
Val Arg Lys Leu Ile Phe Ile Cys Leu Ile Leu Trp Gly Ala Cys Ala
         80                  85                  90 tca ctc gac cgg gat ggt gca caa tat tcc cgc gct ggg cgg gcg atc        399
Ser Leu Asp Arg Asp Gly Ala Gln Tyr Ser Arg Ala Gly Arg Ala Ile
             95                 100                 105 cgc ttt atc ctt ggc gtg gtc gag gcc gca gtc atg ccg gcg atg ctg        447
Arg Phe Ile Leu Gly Val Val Glu Ala Ala Val Met Pro Ala Met Leu
110                 115                 120                 125 ata tac atc agc aac tgg ttt acc aaa tcc gaa cgc tcg cgc gcc aat        495
Ile Tyr Ile Ser Asn Trp Phe Thr Lys Ser Glu Arg Ser Arg Ala Asn
                130                 135                 140 acc ttc ctg atc ctc ggc aac ccg gtg acg gtg ctg tgg atg tcg gtg        543
Thr Phe Leu Ile Leu Gly Asn Pro Val Thr Val Leu Trp Met Ser Val
            145                 150                 155 gtc tcc ggc tac ctg att cag gct ttc ggc tgg cgg gag atg ttt att        591
Val Ser Gly Tyr Leu Ile Gln Ala Phe Gly Trp Arg Glu Met Phe Ile
        160                 165                 170 att gaa ggc gtt ccg gcg gtg att tgg gcc ttc tgc tgg tgg gtg ctg        639
Ile Glu Gly Val Pro Ala Val Ile Trp Ala Phe Cys Trp Trp Val Leu
    175                 180                 185 gta aaa gat aaa ccg tct cag gtc aac tgg ctg gcg gaa agc gaa aag        687
Val Lys Asp Lys Pro Ser Gln Val Asn Trp Leu Ala Glu Ser Glu Lys
190                 195                 200                 205 gcc gca ttg cag gag cag ctg gag cgc gaa cag cag ggt atc aaa ccg        735
Ala Ala Leu Gln Glu Gln Leu Glu Arg Glu Gln Gln Gly Ile Lys Pro
                210                 215                 220 gtg cgc aac tac ggt gag gcc ttc cgc tcg cgt aac gtg gtc ctg ctg        783
Val Arg Asn Tyr Gly Glu Ala Phe Arg Ser Arg Asn Val Val Leu Leu
            225                 230                 235 tgc atg caa tat ttc gcc tgg agc atc ggg gtt tac ggt ttc gtg ctg        831
Cys Met Gln Tyr Phe Ala Trp Ser Ile Gly Val Tyr Gly Phe Val Leu
        240                 245                 250 tgg ctg ccg tca att atc cgc agc ggc ggc gag aat atg ggc atg gtc        879
Trp Leu Pro Ser Ile Ile Arg Ser Gly Gly Glu Asn Met Gly Met Val
    255                 260                 265 gag gtc ggc tgg ctc tca tcc gtc ccc tac ctg gcg gca acc atc gcc        927
Glu Val Gly Trp Leu Ser Ser Val Pro Tyr Leu Ala Ala Thr Ile Ala
270                 275                 280                 285 atg atc gtg gtc tcc tgg gcc tcc gat aaa atg cag aac cgc aag cta        975
Met Ile Val Val Ser Trp Ala Ser Asp Lys Met Gln Asn Arg Lys Leu
                290                 295                 300 ttc gtc tgg ccg ctg ctg ctg att gcc gcc ttc gcg ttt att ggc tcc       1023
Phe Val Trp Pro Leu Leu Leu Ile Ala Ala Phe Ala Phe Ile Gly Ser
            305                 310                 315 tgg gcc gtc ggc gct aac cat ttc tgg gtc tct tat acc ctg ctg gtc       1071
Trp Ala Val Gly Ala Asn His Phe Trp Val Ser Tyr Thr Leu Leu Val
        320                 325                 330 att gcc ggc gcg gcg atg tac gcc ccc tac ggg ccg ttc ttc gcc atc       1119
Ile Ala Gly Ala Ala Met Tyr Ala Pro Tyr Gly Pro Phe Phe Ala Ile
    335                 340                 345 att ccc gag atg ctg ccg cgt aac gtc gcc ggg ggc gcc atg gcg ctg       1167
Ile Pro Glu Met Leu Pro Arg Asn Val Ala Gly Gly Ala Met Ala Leu
350                 355                 360                 365
```

```
att aac agc atg ggc gcg ctg ggt tca ttc ttt ggc tca tgg ttt gtc    1215
Ile Asn Ser Met Gly Ala Leu Gly Ser Phe Phe Gly Ser Trp Phe Val
            370                 375                 380 ggc tac ctg aac ggc acc acc ggc agc ccg tca gcc tcg tac att ttt    1263
Gly Tyr Leu Asn Gly Thr Thr Gly Ser Pro Ser Ala Ser Tyr Ile Phe
        385                 390                 395 atg gga gtg gcg ctt ttc gtc tcg gta tgg ctt act ttg att gtt aag    1311
Met Gly Val Ala Leu Phe Val Ser Val Trp Leu Thr Leu Ile Val Lys
    400                 405                 410 cct gct aat aat caa aaa ctt ccg ctc ggc gca cgt cac gcc              1353
Pro Ala Asn Asn Gln Lys Leu Pro Leu Gly Ala Arg His Ala
415                 420                 425 tgaaacatta acgcaacgga gaaccgcatg aagccgtcag tcattctcta caaaacgctt   1413
cccgacgacc tgcaacaagc gtctggaaca acactttacc gtcacgcagg tgaaaaacct   1473
gcgtt                                                               1478

<210> SEQ ID NO 6
<211> LENGTH: 427
<212> TYPE: PRT
<213> ORGANISM: Klebsiella oxytoca

<400> SEQUENCE: 6

Met Asn Ser Ser Thr Asn Ala Thr Lys Arg Trp Trp Tyr Ile Met Pro
1               5                   10                  15

Ile Val Phe Ile Thr Tyr Ser Leu Ala Tyr Leu Asp Arg Ala Asn Phe
            20                  25                  30

Ser Phe Ala Ser Ala Ala Gly Ile Thr Glu Asp Leu Gly Ile Thr Lys
        35                  40                  45

Gly Ile Ser Ser Leu Leu Gly Ala Leu Phe Phe Leu Gly Tyr Phe Phe
    50                  55                  60

Phe Gln Ile Pro Gly Ala Ile Tyr Ala Glu Arg Arg Ser Val Arg Lys
65                  70                  75                  80

Leu Ile Phe Ile Cys Leu Ile Leu Trp Gly Ala Cys Ala Ser Leu Asp
                85                  90                  95

Arg Asp Gly Ala Gln Tyr Ser Arg Ala Gly Arg Ala Ile Arg Phe Ile
            100                 105                 110

Leu Gly Val Val Glu Ala Ala Val Met Pro Ala Met Leu Ile Tyr Ile
        115                 120                 125

Ser Asn Trp Phe Thr Lys Ser Glu Arg Ser Arg Ala Asn Thr Phe Leu
    130                 135                 140

Ile Leu Gly Asn Pro Val Thr Val Leu Trp Met Ser Val Val Ser Gly
145                 150                 155                 160

Tyr Leu Ile Gln Ala Phe Gly Trp Arg Glu Met Phe Ile Ile Glu Gly
                165                 170                 175

Val Pro Ala Val Ile Trp Ala Phe Cys Trp Trp Val Leu Val Lys Asp
            180                 185                 190

Lys Pro Ser Gln Val Asn Trp Leu Ala Glu Ser Glu Lys Ala Ala Leu
        195                 200                 205

Gln Glu Gln Leu Glu Arg Gln Gln Gly Ile Lys Pro Val Arg Asn
    210                 215                 220

Tyr Gly Glu Ala Phe Arg Ser Arg Asn Val Val Leu Leu Cys Met Gln
225                 230                 235                 240

Tyr Phe Ala Trp Ser Ile Gly Val Tyr Gly Phe Val Leu Trp Leu Pro
                245                 250                 255

Ser Ile Ile Arg Ser Gly Gly Glu Asn Met Gly Met Val Glu Val Gly
```

```
                    260              265                270
Trp Leu Ser Ser Val Pro Tyr Leu Ala Ala Thr Ile Ala Met Ile Val
            275              280              285
Val Ser Trp Ala Ser Asp Lys Met Gln Asn Arg Lys Leu Phe Val Trp
        290              295              300
Pro Leu Leu Ile Ala Ala Phe Ala Phe Ile Gly Ser Trp Ala Val
305              310              315              320
Gly Ala Asn His Phe Trp Val Ser Tyr Thr Leu Leu Val Ile Ala Gly
                325              330              335
Ala Ala Met Tyr Ala Pro Tyr Gly Pro Phe Ala Ile Ile Pro Glu
            340              345              350
Met Leu Pro Arg Asn Val Ala Gly Gly Ala Met Ala Leu Ile Asn Ser
            355              360              365
Met Gly Ala Leu Gly Ser Phe Phe Gly Ser Trp Phe Val Gly Tyr Leu
    370              375              380
Asn Gly Thr Thr Gly Ser Pro Ser Ala Ser Tyr Ile Phe Met Gly Val
385              390              395              400
Ala Leu Phe Val Ser Val Trp Leu Thr Leu Ile Val Lys Pro Ala Asn
                405              410              415
Asn Gln Lys Leu Pro Leu Gly Ala Arg His Ala
            420              425
```

<210> SEQ ID NO 7
<211> LENGTH: 1600
<212> TYPE: DNA
<213> ORGANISM: Pantoea citrea
<220> FEATURE:
<221> NAME/KEY: CDS
<222> LOCATION: (214)...(1521)

<400> SEQUENCE: 7

```
tctgagcttt tcccgacctt atccctgtca gatccctgcc tggttcacga accttgtaac     60
acactttctt aacatgccct tacgtgaccc tgatcccaca ctgtcagtgc aaaaacacgt    120
tttatagctc ctgataagca cagttcgcag cgcgtaactg cacccgcagg ttctgctttt    180
gcgtcaactg acaaaacaga aagggatat atc atg caa aaa tca cag ccg gga     234
                                   Met Gln Lys Ser Gln Pro Gly
                                    1               5 acc cgc tgg ttt cgg att att gtg ccg atc ctg ata gcc tgc atc atg     282
Thr Arg Trp Phe Arg Ile Ile Val Pro Ile Leu Ile Ala Cys Ile Met
        10                  15                  20 tcg ttt atg gat cgg gta aat atc agt ttc gca ttg ccg ggc ggt atg     330
Ser Phe Met Asp Arg Val Asn Ile Ser Phe Ala Leu Pro Gly Gly Met
    25                  30                  35 gag cag gat ctg ctg atg tcc agc cag atg gcc ggg gta gtt agc ggt     378
Glu Gln Asp Leu Leu Met Ser Ser Gln Met Ala Gly Val Val Ser Gly
40                  45                  50                  55 att ttc ttt att ggt tat ctg ttt ttg cag gtt cct ggt ggg cat atc     426
Ile Phe Phe Ile Gly Tyr Leu Phe Leu Gln Val Pro Gly Gly His Ile
                60                  65                  70 gca gta cgt ggc agt ggt aaa cgt ttt att gcc tgg tcg ctt gtt gcc     474
Ala Val Arg Gly Ser Gly Lys Arg Phe Ile Ala Trp Ser Leu Val Ala
            75                  80                  85 tgg gcc gtt gtt tct gtc gct acc ggg ttt gtg act cat cag tac cag     522
Trp Ala Val Val Ser Val Ala Thr Gly Phe Val Thr His Gln Tyr Gln
        90                  95                 100 ctg ttg att tta cgt ttt gca ctg ggg gtc tct gaa ggt ggg atg ttg     570
Leu Leu Ile Leu Arg Phe Ala Leu Gly Val Ser Glu Gly Gly Met Leu
```

-continued

|  |  |  |  |  |  |  |  |  |  |  |  |  |  |  |  |
|---|---|---|---|---|---|---|---|---|---|---|---|---|---|---|---|
|  |  | 105 |  |  |  | 110 |  |  |  | 115 |  |  |  |  |  |
| ccg | gta | gtt | ctg | aca | atg | gtc | agc | aac | tgg | ttt | cct | gaa | aaa | gag | ctg | 618 |
| Pro | Val | Val | Leu | Thr | Met | Val | Ser | Asn | Trp | Phe | Pro | Glu | Lys | Glu | Leu |
| 120 |  |  |  |  | 125 |  |  |  |  | 130 |  |  |  |  | 135 |
| ggg | cgt | gct | aat | gca | ttt | gtc | atg | atg | ttc | gcc | ccg | ctt | ggc | gga | atg | 666 |
| Gly | Arg | Ala | Asn | Ala | Phe | Val | Met | Met | Phe | Ala | Pro | Leu | Gly | Gly | Met |
|  |  |  | 140 |  |  |  |  | 145 |  |  |  |  | 150 |
| att | acc | gcc | cct | gtc | tcc | gga | tgg | att | att | gca | ctg | cta | gac | tgg | cgc | 714 |
| Ile | Thr | Ala | Pro | Val | Ser | Gly | Trp | Ile | Ile | Ala | Leu | Leu | Asp | Trp | Arg |
|  |  |  | 155 |  |  |  |  | 160 |  |  |  |  | 165 |
| tgg | tta | ttt | att | atc | gaa | gga | tta | ctg | tcg | gta | gtg | gtt | ctg | gca | gtc | 762 |
| Trp | Leu | Phe | Ile | Ile | Glu | Gly | Leu | Leu | Ser | Val | Val | Val | Leu | Ala | Val |
|  |  | 170 |  |  |  |  | 175 |  |  |  |  | 180 |
| tgg | tgg | ctg | atg | gtc | agt | gac | cgc | cct | gaa | gat | gcc | cgt | tgg | ctg | ccg | 810 |
| Trp | Trp | Leu | Met | Val | Ser | Asp | Arg | Pro | Glu | Asp | Ala | Arg | Trp | Leu | Pro |
|  | 185 |  |  |  |  | 190 |  |  |  |  | 195 |
| gca | gca | gaa | cgg | gaa | tat | ctg | ctg | cgc | gaa | atg | gcc | cgt | gac | aag | gcc | 858 |
| Ala | Ala | Glu | Arg | Glu | Tyr | Leu | Leu | Arg | Glu | Met | Ala | Arg | Asp | Lys | Ala |
| 200 |  |  |  |  | 205 |  |  |  |  | 210 |  |  |  |  | 215 |
| gag | cgg | agc | aaa | ctc | cct | ccg | atc | agt | cat | gct | ccc | ctg | caa | gag | gtt | 906 |
| Glu | Arg | Ser | Lys | Leu | Pro | Pro | Ile | Ser | His | Ala | Pro | Leu | Gln | Glu | Val |
|  |  |  | 220 |  |  |  |  | 225 |  |  |  |  | 230 |
| ttc | cat | aac | ccg | ggc | ctg | atg | aag | tta | gtg | att | ctg | aac | ttt | ttc | tat | 954 |
| Phe | His | Asn | Pro | Gly | Leu | Met | Lys | Leu | Val | Ile | Leu | Asn | Phe | Phe | Tyr |
|  |  | 235 |  |  |  |  | 240 |  |  |  |  | 245 |
| cag | aca | ggt | gat | tac | gga | tac | act | ctg | tgg | ctg | ccg | act | att | atc | aaa | 1002 |
| Gln | Thr | Gly | Asp | Tyr | Gly | Tyr | Thr | Leu | Trp | Leu | Pro | Thr | Ile | Ile | Lys |
|  |  | 250 |  |  |  |  | 255 |  |  |  |  | 260 |
| aac | ctg | acc | gga | gct | agt | att | ggt | aac | gtc | ggt | ttg | ctg | aca | gtg | cta | 1050 |
| Asn | Leu | Thr | Gly | Ala | Ser | Ile | Gly | Asn | Val | Gly | Leu | Leu | Thr | Val | Leu |
|  | 265 |  |  |  |  | 270 |  |  |  |  | 275 |
| cct | ttt | atc | gcg | acg | tta | tca | ggg | att | tat | gtc | gtc | tct | tac | ctg | agc | 1098 |
| Pro | Phe | Ile | Ala | Thr | Leu | Ser | Gly | Ile | Tyr | Val | Val | Ser | Tyr | Leu | Ser |
| 280 |  |  |  |  | 285 |  |  |  |  | 290 |  |  |  |  | 295 |
| gat | aaa | acc | ggc | aaa | cgt | cgg | caa | tgg | gtg | atg | att | tct | ctg | ttc | tgt | 1146 |
| Asp | Lys | Thr | Gly | Lys | Arg | Arg | Gln | Trp | Val | Met | Ile | Ser | Leu | Phe | Cys |
|  |  |  | 300 |  |  |  |  | 305 |  |  |  |  | 310 |
| ttt | gcg | gcc | tgc | ctg | ttg | gcc | tca | gtc | ctg | tta | cgt | gaa | ttt | gtg | ctg | 1194 |
| Phe | Ala | Ala | Cys | Leu | Leu | Ala | Ser | Val | Leu | Leu | Arg | Glu | Phe | Val | Leu |
|  |  |  | 315 |  |  |  |  | 320 |  |  |  |  | 325 |
| gct | gct | tat | ctg | gct | ctg | gtg | gct | tgc | ggc | ttt | ttc | ctg | aaa | gca | gcc | 1242 |
| Ala | Ala | Tyr | Leu | Ala | Leu | Val | Ala | Cys | Gly | Phe | Phe | Leu | Lys | Ala | Ala |
|  |  | 330 |  |  |  |  | 335 |  |  |  |  | 340 |
| acc | agc | ccg | ttc | tgg | agt | att | ccg | gga | cgt | att | gca | ccg | ccg | gaa | gca | 1290 |
| Thr | Ser | Pro | Phe | Trp | Ser | Ile | Pro | Gly | Arg | Ile | Ala | Pro | Pro | Glu | Ala |
| 345 |  |  |  |  | 350 |  |  |  |  | 355 |
| gcc | ggt | agt | gcc | cgt | ggt | gta | att | aac | gga | ctg | ggg | aat | ctg | ggc | ggt | 1338 |
| Ala | Gly | Ser | Ala | Arg | Gly | Val | Ile | Asn | Gly | Leu | Gly | Asn | Leu | Gly | Gly |
| 360 |  |  |  |  | 365 |  |  |  |  | 370 |  |  |  |  | 375 |
| ttc | tgc | ggc | ccc | tgg | ctg | gtc | gga | tta | atg | atc | tac | ctg | tac | gga | cag | 1386 |
| Phe | Cys | Gly | Pro | Trp | Leu | Val | Gly | Leu | Met | Ile | Tyr | Leu | Tyr | Gly | Gln |
|  |  |  | 380 |  |  |  |  | 385 |  |  |  |  | 390 |
| aat | gca | gcc | gtt | gtt | act | ctg | gca | ggc | tct | ctg | atc | att | gcc | ggg | att | 1434 |
| Asn | Ala | Ala | Val | Val | Thr | Leu | Ala | Gly | Ser | Leu | Ile | Ile | Ala | Gly | Ile |
|  |  | 395 |  |  |  |  | 400 |  |  |  |  | 405 |
| att | gcg | gca | tta | ctg | cca | acg | cag | tgt | gat | ctg | cgc | ccg | gca | gag | gca | 1482 |
| Ile | Ala | Ala | Leu | Leu | Pro | Thr | Gln | Cys | Asp | Leu | Arg | Pro | Ala | Glu | Ala |
|  |  | 410 |  |  |  |  | 415 |  |  |  |  | 420 |
| cgg | cag | cag | aat | ttc | acc | cca | cgt | att | cat | gat | gcc | aaa | taatactgtc |  | | 1531 |

```
Arg Gln Gln Asn Phe Thr Pro Arg Ile His Asp Ala Lys
    425                 430                 435 acccggtaac gctgttgccg ggtgcagcct tcacctttca gggcgtattt ttctgataac    1591
cccgtgtaa                                                            1600

<210> SEQ ID NO 8
<211> LENGTH: 436
<212> TYPE: PRT
<213> ORGANISM: Pantoea citrea

<400> SEQUENCE: 8

Met Gln Lys Ser Gln Pro Gly Thr Arg Trp Phe Arg Ile Ile Val Pro
 1               5                  10                  15

Ile Leu Ile Ala Cys Ile Met Ser Phe Met Asp Arg Val Asn Ile Ser
            20                  25                  30

Phe Ala Leu Pro Gly Gly Met Glu Gln Asp Leu Leu Met Ser Ser Gln
        35                  40                  45

Met Ala Gly Val Val Ser Gly Ile Phe Phe Ile Gly Tyr Leu Phe Leu
    50                  55                  60

Gln Val Pro Gly Gly His Ile Ala Val Arg Gly Ser Gly Lys Arg Phe
65                  70                  75                  80

Ile Ala Trp Ser Leu Val Ala Trp Ala Val Ser Val Ala Thr Gly
                85                  90                  95

Phe Val Thr His Gln Tyr Gln Leu Leu Ile Leu Arg Phe Ala Leu Gly
                100                 105                 110

Val Ser Glu Gly Gly Met Leu Pro Val Val Leu Thr Met Val Ser Asn
            115                 120                 125

Trp Phe Pro Glu Lys Glu Leu Gly Arg Ala Asn Ala Phe Val Met Met
    130                 135                 140

Phe Ala Pro Leu Gly Gly Met Ile Thr Ala Pro Val Ser Gly Trp Ile
145                 150                 155                 160

Ile Ala Leu Leu Asp Trp Arg Trp Leu Phe Ile Ile Glu Gly Leu Leu
                165                 170                 175

Ser Val Val Leu Ala Val Trp Trp Leu Met Val Ser Asp Arg Pro
            180                 185                 190

Glu Asp Ala Arg Trp Leu Pro Ala Ala Glu Arg Glu Tyr Leu Leu Arg
    195                 200                 205

Glu Met Ala Arg Asp Lys Ala Glu Arg Ser Lys Leu Pro Pro Ile Ser
210                 215                 220

His Ala Pro Leu Gln Glu Val Phe His Asn Pro Gly Leu Met Lys Leu
225                 230                 235                 240

Val Ile Leu Asn Phe Phe Tyr Gln Thr Gly Asp Tyr Gly Tyr Thr Leu
                245                 250                 255

Trp Leu Pro Thr Ile Ile Lys Asn Leu Thr Gly Ala Ser Ile Gly Asn
            260                 265                 270

Val Gly Leu Leu Thr Val Leu Pro Phe Ile Ala Thr Leu Ser Gly Ile
        275                 280                 285

Tyr Val Val Ser Tyr Leu Ser Asp Lys Thr Gly Lys Arg Arg Gln Trp
    290                 295                 300

Val Met Ile Ser Leu Phe Cys Phe Ala Ala Cys Leu Leu Ala Ser Val
305                 310                 315                 320

Leu Leu Arg Glu Phe Val Leu Ala Ala Tyr Leu Ala Leu Val Ala Cys
                325                 330                 335

Gly Phe Phe Leu Lys Ala Ala Thr Ser Pro Phe Trp Ser Ile Pro Gly
```

-continued

```
                    340                 345                 350
Arg Ile Ala Pro Pro Glu Ala Ala Gly Ser Ala Arg Gly Val Ile Asn
            355                 360                 365
Gly Leu Gly Asn Leu Gly Gly Phe Cys Gly Pro Trp Leu Val Gly Leu
    370                 375                 380
Met Ile Tyr Leu Tyr Gly Gln Asn Ala Ala Val Val Thr Leu Ala Gly
385                 390                 395                 400
Ser Leu Ile Ile Ala Gly Ile Ile Ala Ala Leu Leu Pro Thr Gln Cys
                405                 410                 415
Asp Leu Arg Pro Ala Glu Ala Arg Gln Gln Asn Phe Thr Pro Arg Ile
            420                 425                 430
His Asp Ala Lys
        435

<210> SEQ ID NO 9
<211> LENGTH: 1500
<212> TYPE: DNA
<213> ORGANISM: Pantoea citrea
<220> FEATURE:
<221> NAME/KEY: CDS
<222> LOCATION: (154)...(1440)

<400> SEQUENCE: 9
tcagctcagg cctcggattt cgttaacggt catgtcttat ttgtcgacgg cggaatgctg      60
gcctcagtat aaaatacagg ggcagacgga atcagagttt gccctgaaga tatcttactg     120 gttgccccctt cggcacacac aggatgttcc ccc atg aat aca agc aga aaa ctg     174
                                    Met Asn Thr Ser Arg Lys Leu
                                    1               5 ccg gtg aaa cgc tgg tgg tat tta atg ccg gtg att ttt att act tac      222
Pro Val Lys Arg Trp Trp Tyr Leu Met Pro Val Ile Phe Ile Thr Tyr
        10                  15                  20 agc ctg gca tat ctg gat cgg gcc aac tac ggc ttt gct gct gcc tct      270
Ser Leu Ala Tyr Leu Asp Arg Ala Asn Tyr Gly Phe Ala Ala Ala Ser
    25                  30                  35 ggg att gaa gca gat ctt gga att agc cgt ggc acc tcc tct ctg att      318
Gly Ile Glu Ala Asp Leu Gly Ile Ser Arg Gly Thr Ser Ser Leu Ile
40                  45                  50                  55 gga gca ctg ttc ttt ctc ggc tac ttc att ttt cag gtg ccc ggg gca      366
Gly Ala Leu Phe Phe Leu Gly Tyr Phe Ile Phe Gln Val Pro Gly Ala
                60                  65                  70 att tat gca gtg aaa cgc agt gtc cgt aaa ctg gtg ttt acc agc ctg      414
Ile Tyr Ala Val Lys Arg Ser Val Arg Lys Leu Val Phe Thr Ser Leu
            75                  80                  85 ctg ttg tgg gga ttt tgt gcc gct gcg acc gga ctt atc agc aat att      462
Leu Leu Trp Gly Phe Cys Ala Ala Ala Thr Gly Leu Ile Ser Asn Ile
        90                  95                  100 ccg gct ctg atg gtg atc cgc ttt gtt ctg ggt gtt gtt gaa gcc gca      510
Pro Ala Leu Met Val Ile Arg Phe Val Leu Gly Val Val Glu Ala Ala
    105                 110                 115 gtg atg cca gcg atg ctg att tac atc agc aac tgg ttc acc cgt cag      558
Val Met Pro Ala Met Leu Ile Tyr Ile Ser Asn Trp Phe Thr Arg Gln
120                 125                 130                 135 gaa cgt tca cgg gct aat acc ttt ctg gta tta ggt aac ccg gtc acg      606
Glu Arg Ser Arg Ala Asn Thr Phe Leu Val Leu Gly Asn Pro Val Thr
                140                 145                 150 gtg tta tgg atg tct att gtt tcc gga tat ctg atc aat gct ttt ggc      654
Val Leu Trp Met Ser Ile Val Ser Gly Tyr Leu Ile Asn Ala Phe Gly
            155                 160                 165
```

```
tgg cgg gaa atg ttt att ttc gag ggt gtg cct gcc tta atc tgg gcc      702
Trp Arg Glu Met Phe Ile Phe Glu Gly Val Pro Ala Leu Ile Trp Ala
        170                 175                 180 atc ttc tgg tgg ttt att gtc cgg gac aaa ccg gag cag gtg agc tgg      750
Ile Phe Trp Trp Phe Ile Val Arg Asp Lys Pro Glu Gln Val Ser Trp
185                 190                 195 ctg aca gaa aca gaa aag cag caa ctg gcc agt gca atg gct gaa gag      798
Leu Thr Glu Thr Glu Lys Gln Gln Leu Ala Ser Ala Met Ala Glu Glu
200                 205                 210                 215 cag cag gca ata cca ccg atg cgc aat gtg ccg cag gcc ctg cgt tcc      846
Gln Gln Ala Ile Pro Pro Met Arg Asn Val Pro Gln Ala Leu Arg Ser
                220                 225                 230 cgc aat gtg gtg gta ctg tgc ctg tta cac gct ctg tgg agc atc gga      894
Arg Asn Val Val Val Leu Cys Leu Leu His Ala Leu Trp Ser Ile Gly
            235                 240                 245 gtg tat ggt ttt atg atg tgg atg cca tcg ata ctg cgt agc gct gca      942
Val Tyr Gly Phe Met Met Trp Met Pro Ser Ile Leu Arg Ser Ala Ala
        250                 255                 260 tca atg gac att gtc cgg gta ggc tgg ctg gcc gca gtt ccg tat ctg      990
Ser Met Asp Ile Val Arg Val Gly Trp Leu Ala Ala Val Pro Tyr Leu
265                 270                 275 gcc gcg att att act atg ctg gtg att tca tgg ctg tca gat aaa acc     1038
Ala Ala Ile Ile Thr Met Leu Val Ile Ser Trp Leu Ser Asp Lys Thr
280                 285                 290                 295 ggg ctg cgt cgg ctt ttt atc tgg cca tta ttg ctg att gcg tca gtt     1086
Gly Leu Arg Arg Leu Phe Ile Trp Pro Leu Leu Leu Ile Ala Ser Val
                300                 305                 310 act ttt ttt ggg tcc tgg tta ctt ggg agc tac tca ttc tgg ttt tcc     1134
Thr Phe Phe Gly Ser Trp Leu Leu Gly Ser Tyr Ser Phe Trp Phe Ser
            315                 320                 325 tat ggc ttg ctg gta ctg gct gct gct tgt atg tat gcc ccg tat gga     1182
Tyr Gly Leu Leu Val Leu Ala Ala Ala Cys Met Tyr Ala Pro Tyr Gly
        330                 335                 340 ccg ttt ttt gcg ttg att cct gaa ttg ctg cca aaa aat gtg gcg ggg     1230
Pro Phe Phe Ala Leu Ile Pro Glu Leu Leu Pro Lys Asn Val Ala Gly
345                 350                 355 att tct atc ggg tta att aac tgt tgc ggg gcg ctg gga gct ttt gcc     1278
Ile Ser Ile Gly Leu Ile Asn Cys Cys Gly Ala Leu Gly Ala Phe Ala
360                 365                 370                 375 gga gcc tgg ctg gtg ggc tat ctt aat ggt ctg acc ggt ggt ccg ggg     1326
Gly Ala Trp Leu Val Gly Tyr Leu Asn Gly Leu Thr Gly Gly Pro Gly
                380                 385                 390 gct tct tac act ttt atg gcc att gca ttg ctg gtt tct gta ggg ttg     1374
Ala Ser Tyr Thr Phe Met Ala Ile Ala Leu Leu Val Ser Val Gly Leu
            395                 400                 405 gtg ttt ttc ctg aaa gtc cct tca ggg aat ttg gtc act cgt cgg ttg     1422
Val Phe Phe Leu Lys Val Pro Ser Gly Asn Leu Val Thr Arg Arg Leu
        410                 415                 420 ctg aaa ggt gat gca aag taaaaggaat agcgatgaaa cggaacagga            1470
Leu Lys Gly Asp Ala Lys
        425 tgtctttgca ggatattgcg gacctcgccg                                    1500

<210> SEQ ID NO 10
<211> LENGTH: 429
<212> TYPE: PRT
<213> ORGANISM: Pantoea citrea

<400> SEQUENCE: 10

Met Asn Thr Ser Arg Lys Leu Pro Val Lys Arg Trp Trp Tyr Leu Met
```

-continued

```
  1               5                  10                 15
Pro Val Ile Phe Ile Thr Tyr Ser Leu Ala Tyr Leu Asp Arg Ala Asn
             20                  25                 30

Tyr Gly Phe Ala Ala Ala Ser Gly Ile Glu Ala Asp Leu Gly Ile Ser
             35                  40                 45

Arg Gly Thr Ser Ser Leu Ile Gly Ala Leu Phe Phe Leu Gly Tyr Phe
 50                      55                 60

Ile Phe Gln Val Pro Gly Ala Ile Tyr Ala Val Lys Arg Ser Val Arg
 65                      70                 75                 80

Lys Leu Val Phe Thr Ser Leu Leu Leu Trp Gly Phe Cys Ala Ala Ala
             85                  90                 95

Thr Gly Leu Ile Ser Asn Ile Pro Ala Leu Met Val Ile Arg Phe Val
            100                 105                110

Leu Gly Val Val Glu Ala Ala Val Met Pro Ala Met Leu Ile Tyr Ile
            115                 120                125

Ser Asn Trp Phe Thr Arg Gln Glu Arg Ser Arg Ala Asn Thr Phe Leu
            130                 135                140

Val Leu Gly Asn Pro Val Thr Val Leu Trp Met Ser Ile Val Ser Gly
145                     150                 155                160

Tyr Leu Ile Asn Ala Phe Gly Trp Arg Glu Met Phe Ile Phe Glu Gly
            165                 170                175

Val Pro Ala Leu Ile Trp Ala Ile Phe Trp Phe Ile Val Arg Asp
            180                 185                190

Lys Pro Glu Gln Val Ser Trp Leu Thr Glu Thr Glu Lys Gln Gln Leu
            195                 200                205

Ala Ser Ala Met Ala Glu Glu Gln Gln Ala Ile Pro Pro Met Arg Asn
210                     215                 220

Val Pro Gln Ala Leu Arg Ser Arg Asn Val Val Leu Cys Leu Leu
225                     230                 235                240

His Ala Leu Trp Ser Ile Gly Val Tyr Gly Phe Met Trp Met Pro
            245                 250                255

Ser Ile Leu Arg Ser Ala Ala Ser Met Asp Ile Val Arg Val Gly Trp
            260                 265                270

Leu Ala Ala Val Pro Tyr Leu Ala Ala Ile Ile Thr Met Leu Val Ile
            275                 280                285

Ser Trp Leu Ser Asp Lys Thr Gly Leu Arg Arg Leu Phe Ile Trp Pro
            290                 295                300

Leu Leu Leu Ile Ala Ser Val Thr Phe Gly Ser Trp Leu Leu Gly
305                     310                 315                320

Ser Tyr Ser Phe Trp Phe Ser Tyr Gly Leu Leu Val Leu Ala Ala Ala
            325                 330                335

Cys Met Tyr Ala Pro Tyr Gly Pro Phe Phe Ala Leu Ile Pro Glu Leu
            340                 345                350

Leu Pro Lys Asn Val Ala Gly Ile Ser Ile Gly Leu Ile Asn Cys Cys
            355                 360                365

Gly Ala Leu Gly Ala Phe Ala Gly Ala Trp Leu Val Gly Tyr Leu Asn
370                     375                 380

Gly Leu Thr Gly Gly Pro Gly Ala Ser Tyr Thr Phe Met Ala Ile Ala
385                     390                 395                400

Leu Leu Val Ser Val Gly Leu Val Phe Phe Leu Lys Val Pro Ser Gly
            405                 410                415

Asn Leu Val Thr Arg Arg Leu Leu Lys Gly Asp Ala Lys
            420                 425
```

<210> SEQ ID NO 11
<211> LENGTH: 1500
<212> TYPE: DNA
<213> ORGANISM: Klebsiella oxytoca
<220> FEATURE:
<221> NAME/KEY: CDS
<222> LOCATION: (70)...(1386)

<400> SEQUENCE: 11

```
ctaaaacaag cacaataata ataatcacct tcatcaccag aatattttta atattacgag      60 actataaag atg aat ata acc tct aac tct aca acc aaa gat ata ccg cgc    111
         Met Asn Ile Thr Ser Asn Ser Thr Thr Lys Asp Ile Pro Arg
          1               5                  10 cag cgc tgg tta aga atc att ccg cct ata ctg atc act tgt att att      159
Gln Arg Trp Leu Arg Ile Ile Pro Pro Ile Leu Ile Thr Cys Ile Ile
 15                  20                  25                  30 tct tat atg gac cgg gtc aat att gcc ttt gcg atg ccc gga ggt atg      207
Ser Tyr Met Asp Arg Val Asn Ile Ala Phe Ala Met Pro Gly Gly Met
                 35                  40                  45 gat gcc gac tta ggt att tcc gcc acc atg gcg ggg ctg gcg ggc ggt      255
Asp Ala Asp Leu Gly Ile Ser Ala Thr Met Ala Gly Leu Ala Gly Gly
             50                  55                  60 att ttc ttt atc ggt tat cta ttt tta cag gtt ccc ggc ggg aaa att      303
Ile Phe Phe Ile Gly Tyr Leu Phe Leu Gln Val Pro Gly Gly Lys Ile
         65                  70                  75 gcc gtt cac ggt agc ggt aag aaa ttt atc ggc tgg tcg ctg gtc gcc      351
Ala Val His Gly Ser Gly Lys Lys Phe Ile Gly Trp Ser Leu Val Ala
     80                  85                  90 tgg gcg gtc atc tcc gtg ctg acg ggg tta att acc aat cag tac cag      399
Trp Ala Val Ile Ser Val Leu Thr Gly Leu Ile Thr Asn Gln Tyr Gln
 95                 100                 105                 110 ctg ctg gcc ctg cgc ttc tta ctg ggc gtg gcg gaa ggc ggt atg ctg      447
Leu Leu Ala Leu Arg Phe Leu Leu Gly Val Ala Glu Gly Gly Met Leu
                115                 120                 125 ccg gtc gtt ctc acg atg atc agt aac tgg ttc ccc gac gct gaa cgc      495
Pro Val Val Leu Thr Met Ile Ser Asn Trp Phe Pro Asp Ala Glu Arg
            130                 135                 140 ggt cgc gcc aac gcg att gtc att atg ttt gtg ccg att gcc ggg att      543
Gly Arg Ala Asn Ala Ile Val Ile Met Phe Val Pro Ile Ala Gly Ile
        145                 150                 155 atc acc gcc cca ctc tca ggc tgg att atc acg gtt ctc gac tgg cgc      591
Ile Thr Ala Pro Leu Ser Gly Trp Ile Ile Thr Val Leu Asp Trp Arg
    160                 165                 170 tgg ctg ttt att atc gaa ggt ttg ctc tcg ctg gtt gtt ctg gtt ctg      639
Trp Leu Phe Ile Ile Glu Gly Leu Leu Ser Leu Val Val Leu Val Leu
175                 180                 185                 190 tgg gca tac acc atc tat gac cgt ccg cag gaa gcg cgc tgg att tcc      687
Trp Ala Tyr Thr Ile Tyr Asp Arg Pro Gln Glu Ala Arg Trp Ile Ser
                195                 200                 205 gaa gca gag aag cgc tat ctg gtc gag acg ctg gcc gcg gag caa aaa      735
Glu Ala Glu Lys Arg Tyr Leu Val Glu Thr Leu Ala Ala Glu Gln Lys
            210                 215                 220 gcc att gcc ggc acc gag gtg aaa aac gcc tct ctg agc gcc gtt ctc      783
Ala Ile Ala Gly Thr Glu Val Lys Asn Ala Ser Leu Ser Ala Val Leu
        225                 230                 235 tcc gac aaa acc atg tgg cag ctt atc gcc ctg aac ttc ttc tac cag      831
Ser Asp Lys Thr Met Trp Gln Leu Ile Ala Leu Asn Phe Phe Tyr Gln
    240                 245                 250 acc ggc att tac ggc tac acc ctg tgg cta ccc acc att ctg aaa gaa      879
Thr Gly Ile Tyr Gly Tyr Thr Leu Trp Leu Pro Thr Ile Leu Lys Glu
```

```
Thr Gly Ile Tyr Gly Tyr Thr Leu Trp Leu Pro Thr Ile Leu Lys Glu
255                 260                 265                 270 ttg acc cat agc agc atg ggg cag gtc ggc atg ctt gcc att ctg ccg      927
Leu Thr His Ser Ser Met Gly Gln Val Gly Met Leu Ala Ile Leu Pro
                275                 280                 285 tac gtc ggc gcc att gct ggg atg ttc ctg ttt tcc tcc ctt tca gac      975
Tyr Val Gly Ala Ile Ala Gly Met Phe Leu Phe Ser Ser Leu Ser Asp
            290                 295                 300 cga acc ggt aaa cgc aag ctg ttc gtc tgc ctg ccg ctg att ggc ttc     1023
Arg Thr Gly Lys Arg Lys Leu Phe Val Cys Leu Pro Leu Ile Gly Phe
        305                 310                 315 gct ctg tgc atg ttc ctg tcg gtg gcg ctg aaa aac caa att tgg ctc     1071
Ala Leu Cys Met Phe Leu Ser Val Ala Leu Lys Asn Gln Ile Trp Leu
    320                 325                 330 tcc tat gcc gcg ctg gtc ggc tgc gga ttc ttc ctg caa tcg gcg gct     1119
Ser Tyr Ala Ala Leu Val Gly Cys Gly Phe Phe Leu Gln Ser Ala Ala
335                 340                 345                 350 ggc gtg ttc tgg acc atc ccg gca cgt ctg ttc agc gcg gaa atg gcg     1167
Gly Val Phe Trp Thr Ile Pro Ala Arg Leu Phe Ser Ala Glu Met Ala
                355                 360                 365 ggc ggc gcg cgc ggg gtt atc aac gcg ctt ggc aac ctc ggc gga ttt     1215
Gly Gly Ala Arg Gly Val Ile Asn Ala Leu Gly Asn Leu Gly Gly Phe
            370                 375                 380 tgt ggc cct tat gcg gtc ggg gtg ctg atc acg ttg tac agc aaa gac     1263
Cys Gly Pro Tyr Ala Val Gly Val Leu Ile Thr Leu Tyr Ser Lys Asp
        385                 390                 395 gct ggc gtc tat tgc ctg gcg atc tcc ctg gcg ctg gcc gcg ctg atg     1311
Ala Gly Val Tyr Cys Leu Ala Ile Ser Leu Ala Leu Ala Ala Leu Met
    400                 405                 410 gcg ctg ctg ctg ccg gcg aaa tgc gat gcc ggt gct gcg ccg gta aag     1359
Ala Leu Leu Leu Pro Ala Lys Cys Asp Ala Gly Ala Ala Pro Val Lys
415                 420                 425                 430 acg ata aat cca cat aaa cgc act gcg taaactcgag cccggcggcg           1406
Thr Ile Asn Pro His Lys Arg Thr Ala
                435 ctgcgcctgc cgggcctgcg aaatatgccg ggttcacccg gtaacaatga gatgcgaaag   1466 atgagcaaga aacaggcctt ctggctgggt attg                                1500

<210> SEQ ID NO 12
<211> LENGTH: 439
<212> TYPE: PRT
<213> ORGANISM: Klebsiella oxytoca

<400> SEQUENCE: 12

Met Asn Ile Thr Ser Asn Ser Thr Thr Lys Asp Ile Pro Arg Gln Arg
 1               5                  10                  15

Trp Leu Arg Ile Ile Pro Pro Ile Leu Ile Thr Cys Ile Ile Ser Tyr
            20                  25                  30

Met Asp Arg Val Asn Ile Ala Phe Ala Met Pro Gly Gly Met Asp Ala
        35                  40                  45

Asp Leu Gly Ile Ser Ala Thr Met Ala Gly Leu Ala Gly Gly Ile Phe
    50                  55                  60

Phe Ile Gly Tyr Leu Phe Leu Gln Val Pro Gly Gly Lys Ile Ala Val
65                  70                  75                  80

His Gly Ser Gly Lys Lys Phe Ile Gly Trp Ser Leu Val Ala Trp Ala
                85                  90                  95

Val Ile Ser Val Leu Thr Gly Leu Ile Thr Asn Gln Tyr Gln Leu Leu
            100                 105                 110
```

```
Ala Leu Arg Phe Leu Leu Gly Val Ala Glu Gly Gly Met Leu Pro Val
            115                 120                 125

Val Leu Thr Met Ile Ser Asn Trp Phe Pro Asp Ala Glu Arg Gly Arg
    130                 135                 140

Ala Asn Ala Ile Val Ile Met Phe Val Pro Ile Ala Gly Ile Ile Thr
145                 150                 155                 160

Ala Pro Leu Ser Gly Trp Ile Ile Thr Val Leu Asp Trp Arg Trp Leu
                165                 170                 175

Phe Ile Ile Glu Gly Leu Leu Ser Leu Val Val Leu Val Leu Trp Ala
            180                 185                 190

Tyr Thr Ile Tyr Asp Arg Pro Gln Glu Ala Arg Trp Ile Ser Glu Ala
        195                 200                 205

Glu Lys Arg Tyr Leu Val Glu Thr Leu Ala Ala Glu Gln Lys Ala Ile
    210                 215                 220

Ala Gly Thr Glu Val Lys Asn Ala Ser Leu Ser Ala Val Leu Ser Asp
225                 230                 235                 240

Lys Thr Met Trp Gln Leu Ile Ala Leu Asn Phe Phe Tyr Gln Thr Gly
                245                 250                 255

Ile Tyr Gly Tyr Thr Leu Trp Leu Pro Thr Ile Leu Lys Glu Leu Thr
            260                 265                 270

His Ser Ser Met Gly Gln Val Gly Met Leu Ala Ile Leu Pro Tyr Val
        275                 280                 285

Gly Ala Ile Ala Gly Met Phe Leu Phe Ser Ser Leu Ser Asp Arg Thr
    290                 295                 300

Gly Lys Arg Lys Leu Phe Val Cys Leu Pro Leu Ile Gly Phe Ala Leu
305                 310                 315                 320

Cys Met Phe Leu Ser Val Ala Leu Lys Asn Gln Ile Trp Leu Ser Tyr
                325                 330                 335

Ala Ala Leu Val Gly Cys Gly Phe Phe Leu Gln Ser Ala Ala Gly Val
            340                 345                 350

Phe Trp Thr Ile Pro Ala Arg Leu Phe Ser Ala Glu Met Ala Gly Gly
        355                 360                 365

Ala Arg Gly Val Ile Asn Ala Leu Gly Asn Leu Gly Gly Phe Cys Gly
    370                 375                 380

Pro Tyr Ala Val Gly Val Leu Ile Thr Leu Tyr Ser Lys Asp Ala Gly
385                 390                 395                 400

Val Tyr Cys Leu Ala Ile Ser Leu Ala Leu Ala Leu Met Ala Leu
                405                 410                 415

Leu Leu Pro Ala Lys Cys Asp Ala Gly Ala Ala Pro Val Lys Thr Ile
            420                 425                 430

Asn Pro His Lys Arg Thr Ala
        435

<210> SEQ ID NO 13
<211> LENGTH: 3153
<212> TYPE: DNA
<213> ORGANISM: Unknown
<220> FEATURE:
<223> OTHER INFORMATION: environmental source
<220> FEATURE:
<221> NAME/KEY: CDS
<222> LOCATION: (292)...(1236)
<220> FEATURE:
<221> NAME/KEY: CDS
<222> LOCATION: (1252)...(2280)
<220> FEATURE:
<221> NAME/KEY: CDS
```

-continued

<222> LOCATION: (2293)...(3045)

<400> SEQUENCE: 13

```
catgcctgca ggtcgactct agaggatctc gccgcgcctc aggtcgaggg atacactcgt    60
cagcgctttc gtgccgccga actccttcga acggcacga aactccagaa gtttgtccgt   120
atccaccccg ctcctcccaa agctttatga ggctatagga tattgatatg gtatcgataa   180
cactcctgtc aagaggcgt tttcacgcca ggcgggaggg caaaatagga ctggacaatt   240
ccttcaagcg ggatatgtta tcgataacaa atcatcttcc ggaggagagc c atg agc   297
                                                            Met Ser
                                                              1
```

| | | | | | | | | | | | | | | | | |
|---|---|---|---|---|---|---|---|---|---|---|---|---|---|---|---|---|
| aag | atc | gat | gtg | ttg | cag | gtc | ggt | ccc | tac | cct | gca | tgg | gac | gag | gag | 345 |
| Lys | Ile | Asp | Val | Leu | Gln | Val | Gly | Pro | Tyr | Pro | Ala | Trp | Asp | Glu | Glu | |
| | 5 | | | | 10 | | | | | 15 | | | | | | |

| | | | | | | | | | | | | | | | | |
|---|---|---|---|---|---|---|---|---|---|---|---|---|---|---|---|---|
| cgc | ctg | aac | gcg | acc | ttc | acg | atg | cac | cgc | tat | ttc | gag | gcg | gcc | gac | 393 |
| Arg | Leu | Asn | Ala | Thr | Phe | Thr | Met | His | Arg | Tyr | Phe | Glu | Ala | Ala | Asp | |
| | 20 | | | | 25 | | | | | 30 | | | | | | |

| | | | | | | | | | | | | | | | | |
|---|---|---|---|---|---|---|---|---|---|---|---|---|---|---|---|---|
| aag | gcg | gcg | ttt | ctg | gcc | gag | cac | ggc | ggc | acg | atc | cgc | ggc | atc | gcc | 441 |
| Lys | Ala | Ala | Phe | Leu | Ala | Glu | His | Gly | Gly | Thr | Ile | Arg | Gly | Ile | Ala | |
| 35 | | | | 40 | | | | | 45 | | | | | 50 | | |

| | | | | | | | | | | | | | | | | |
|---|---|---|---|---|---|---|---|---|---|---|---|---|---|---|---|---|
| acg | cgc | ggc | gag | ctt | ggt | gcc | aac | cgg | gcg | atg | atc | gag | gcg | ctg | ccg | 489 |
| Thr | Arg | Gly | Glu | Leu | Gly | Ala | Asn | Arg | Ala | Met | Ile | Glu | Ala | Leu | Pro | |
| | | 55 | | | | | 60 | | | | | 65 | | | | |

| | | | | | | | | | | | | | | | | |
|---|---|---|---|---|---|---|---|---|---|---|---|---|---|---|---|---|
| aag | ctg | gaa | gtg | atc | tcg | gtc | tac | ggc | gtc | ggc | ttc | gat | gcg | gtg | gac | 537 |
| Lys | Leu | Glu | Val | Ile | Ser | Val | Tyr | Gly | Val | Gly | Phe | Asp | Ala | Val | Asp | |
| | | | 70 | | | | | 75 | | | | | 80 | | | |

| | | | | | | | | | | | | | | | | |
|---|---|---|---|---|---|---|---|---|---|---|---|---|---|---|---|---|
| ctt | tcg | gcg | gcc | cgc | gag | cgc | ggc | atc | cgc | gtc | acc | aac | acg | ccc | gac | 585 |
| Leu | Ser | Ala | Ala | Arg | Glu | Arg | Gly | Ile | Arg | Val | Thr | Asn | Thr | Pro | Asp | |
| | | 85 | | | | | 90 | | | | | 95 | | | | |

| | | | | | | | | | | | | | | | | |
|---|---|---|---|---|---|---|---|---|---|---|---|---|---|---|---|---|
| gtg | ctc | acc | aag | gac | gtg | gcc | gat | ctc | ggc | atc | gcc | atg | atg | ctg | gcg | 633 |
| Val | Leu | Thr | Lys | Asp | Val | Ala | Asp | Leu | Gly | Ile | Ala | Met | Met | Leu | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| cag | gcg | cgc | ggc | gtc | atc | ggc | gga | gag | gcc | tgg | gtg | aag | agc | ggc | gat | 681 |
| Gln | Ala | Arg | Gly | Val | Ile | Gly | Gly | Glu | Ala | Trp | Val | Lys | Ser | Gly | Asp | |
| 115 | | | | 120 | | | | | 125 | | | | | 130 | | |

| | | | | | | | | | | | | | | | | |
|---|---|---|---|---|---|---|---|---|---|---|---|---|---|---|---|---|
| tgg | gca | agc | aag | ggt | ctc | tat | ccg | ctg | aag | cgc | cgc | gta | cat | ggc | atg | 729 |
| Trp | Ala | Ser | Lys | Gly | Leu | Tyr | Pro | Leu | Lys | Arg | Arg | Val | His | Gly | Met | |
| | | | 135 | | | | | 140 | | | | | 145 | | | |

| | | | | | | | | | | | | | | | | |
|---|---|---|---|---|---|---|---|---|---|---|---|---|---|---|---|---|
| cgc | gcc | ggg | gtg | ctc | ggc | ctc | ggc | cgc | atc | ggc | tac | gag | gtg | gcc | aag | 777 |
| Arg | Ala | Gly | Val | Leu | Gly | Leu | Gly | Arg | Ile | Gly | Tyr | Glu | Val | Ala | Lys | |
| | | 150 | | | | | 155 | | | | | 160 | | | | |

| | | | | | | | | | | | | | | | | |
|---|---|---|---|---|---|---|---|---|---|---|---|---|---|---|---|---|
| cgc | ctt | gcc | ggc | ttc | gac | atg | gac | atc | gcc | tac | agc | gac | acc | ggc | ccg | 825 |
| Arg | Leu | Ala | Gly | Phe | Asp | Met | Asp | Ile | Ala | Tyr | Ser | Asp | Thr | Gly | Pro | |
| | 165 | | | | | 170 | | | | | 175 | | | | | |

| | | | | | | | | | | | | | | | | |
|---|---|---|---|---|---|---|---|---|---|---|---|---|---|---|---|---|
| aag | gat | ttc | gcc | agg | gac | tgg | acc | ttc | gtc | gcc | gat | ccg | gcg | gag | ctg | 873 |
| Lys | Asp | Phe | Ala | Arg | Asp | Trp | Thr | Phe | Val | Ala | Asp | Pro | Ala | Glu | Leu | |
| 180 | | | | | 185 | | | | | 190 | | | | | | |

| | | | | | | | | | | | | | | | | |
|---|---|---|---|---|---|---|---|---|---|---|---|---|---|---|---|---|
| gcc | gcc | cgc | tcc | gac | ttc | ctc | ttc | gtc | acg | ctc | gcc | gcc | tcc | gcc | gag | 921 |
| Ala | Ala | Arg | Ser | Asp | Phe | Leu | Phe | Val | Thr | Leu | Ala | Ala | Ser | Ala | Glu | |
| 195 | | | | | 200 | | | | | 205 | | | | | 210 | |

| | | | | | | | | | | | | | | | | |
|---|---|---|---|---|---|---|---|---|---|---|---|---|---|---|---|---|
| acg | cgc | cac | atc | gtc | ggc | cgc | aag | gtc | atc | gag | gcg | ctc | ggc | cct | gag | 969 |
| Thr | Arg | His | Ile | Val | Gly | Arg | Lys | Val | Ile | Glu | Ala | Leu | Gly | Pro | Glu | |
| | | | 215 | | | | | 220 | | | | | 225 | | | |

| | | | | | | | | | | | | | | | | |
|---|---|---|---|---|---|---|---|---|---|---|---|---|---|---|---|---|
| ggc | atg | ctg | atc | aac | atc | tcg | cgc | gct | tcc | aac | atc | gat | gaa | agc | gcc | 1017 |
| Gly | Met | Leu | Ile | Asn | Ile | Ser | Arg | Ala | Ser | Asn | Ile | Asp | Glu | Ser | Ala | |
| | | | 230 | | | | | 235 | | | | | 240 | | | |

| | | | | | | | | | | | | | | | | |
|---|---|---|---|---|---|---|---|---|---|---|---|---|---|---|---|---|
| ctt | ctc | gac | gcg | ctg | gag | acg | aag | gcg | ctc | ggc | tcg | gcc | gcg | ctc | gac | 1065 |
| Leu | Leu | Asp | Ala | Leu | Glu | Thr | Lys | Ala | Leu | Gly | Ser | Ala | Ala | Leu | Asp | |
| | | 245 | | | | | 250 | | | | | 255 | | | | |

```
gtc ttc gag ggc gag ccg aac ctc aat ccg cgt ttc ctt gcc ctc gac      1113
Val Phe Glu Gly Glu Pro Asn Leu Asn Pro Arg Phe Leu Ala Leu Asp
260                 265                 270 aac gtc ctc ttg cag ccg cac atg gcc tcc ggc acg atc gag acc cgc      1161
Asn Val Leu Leu Gln Pro His Met Ala Ser Gly Thr Ile Glu Thr Arg
275                 280                 285                 290 aag gcc atg ggc cag ctc gtc ttc gac aac ctg tcg gcc cat ttc gac      1209
Lys Ala Met Gly Gln Leu Val Phe Asp Asn Leu Ser Ala His Phe Asp
                295                 300                 305 ggc cgg ccg ctg ccg acc ccg gtt ctg taaggagaga ggtcc atg aag gcg     1260
Gly Arg Pro Leu Pro Thr Pro Val Leu                 Met Lys Ala
310                 315 atc gtc atc cat cag gcc aag gac ctg cgc gtc gag gac agc gcc gtc      1308
Ile Val Ile His Gln Ala Lys Asp Leu Arg Val Glu Asp Ser Ala Val
320                 325                 330 gag gcg ccc ggc ccc ggc gag gtg gag atc cgc ctt gcc gcc ggc ggc      1356
Glu Ala Pro Gly Pro Gly Glu Val Glu Ile Arg Leu Ala Ala Gly Gly
335                 340                 345                 350 atc tgc ggc tcg gac ctg cac tac tac aac cac ggc ggc ttc ggc acg      1404
Ile Cys Gly Ser Asp Leu His Tyr Tyr Asn His Gly Gly Phe Gly Thr
                355                 360                 365 gtg cgc ctc aag gag ccg atg atc ctc ggc cat gag gtt tcc ggc cac      1452
Val Arg Leu Lys Glu Pro Met Ile Leu Gly His Glu Val Ser Gly His
370                 375                 380 gtc gcg gcg ctc ggc gaa ggc gtc tcc ggc ctt gcc atc ggc gac ctc      1500
Val Ala Ala Leu Gly Glu Gly Val Ser Gly Leu Ala Ile Gly Asp Leu
385                 390                 395 gtc gcc gtc tcg ccc tcg cgg ccc tgc ggg gcg tgc gac tat tgc ctc      1548
Val Ala Val Ser Pro Ser Arg Pro Cys Gly Ala Cys Asp Tyr Cys Leu
400                 405                 410 aag ggc ttg gcg aac cat tgc ttc aac atg cgc ttc tac ggc tcg gcc      1596
Lys Gly Leu Ala Asn His Cys Phe Asn Met Arg Phe Tyr Gly Ser Ala
415                 420                 425                 430 atg ccc ttc ccg cac atc cag ggc gcg ttc cgc gag cgg ctg gtc gcc      1644
Met Pro Phe Pro His Ile Gln Gly Ala Phe Arg Glu Arg Leu Val Ala
                435                 440                 445 aag gcc agc cag tgc gtg aag gct gag ggc ctt tcg gca ggt gaa gcc      1692
Lys Ala Ser Gln Cys Val Lys Ala Glu Gly Leu Ser Ala Gly Glu Ala
                450                 455                 460 gcg atg gcc gag ccg ctc tcc gtc acg ctt cac gcc acg cgc cgg gcc      1740
Ala Met Ala Glu Pro Leu Ser Val Thr Leu His Ala Thr Arg Arg Ala
        465                 470                 475 ggc gaa atg ctg ggc aag cgc gtg ctc gtc acc ggc tgc ggg ccg atc      1788
Gly Glu Met Leu Gly Lys Arg Val Leu Val Thr Gly Cys Gly Pro Ile
480                 485                 490 ggc acc ctg tcg atc ctc gcc gcc cgg cgc gcc ggc gcg gcg gag atc      1836
Gly Thr Leu Ser Ile Leu Ala Ala Arg Arg Ala Gly Ala Ala Glu Ile
495                 500                 505                 510 gtc gcc gct gac ctt tcc gag cgt gca ctc ggc ttt gcc cgc gcc gtc      1884
Val Ala Ala Asp Leu Ser Glu Arg Ala Leu Gly Phe Ala Arg Ala Val
                515                 520                 525 ggc gcg gac cgc acg gtc aac ctg tcg gaa gac cgc gac ggc ctc gtt      1932
Gly Ala Asp Arg Thr Val Asn Leu Ser Glu Asp Arg Asp Gly Leu Val
                530                 535                 540 ccg ttc agc gag aac aag gga tat ttc gat gtc ctc tac gaa tgc tcg      1980
Pro Phe Ser Glu Asn Lys Gly Tyr Phe Asp Val Leu Tyr Glu Cys Ser
                545                 550                 555 ggc gcc cag ccg gcg ctg gtt gcc ggc atc cag gcc ttg cgc ccg cgc      2028
Gly Ala Gln Pro Ala Leu Val Ala Gly Ile Gln Ala Leu Arg Pro Arg
```

-continued

| | | |
|---|---|---|
| ggc gtc atc gtc cag ctc ggc ctc ggc ggc gag atg agc ctt ccc atg<br>Gly Val Ile Val Gln Leu Gly Leu Gly Gly Glu Met Ser Leu Pro Met<br>575                 580                 585                 590 | 2076 |
| atg gcg atc acc gcc aag gaa ctg gac ctg cgc ggc tcc ttc cgc ttc<br>Met Ala Ile Thr Ala Lys Glu Leu Asp Leu Arg Gly Ser Phe Arg Phe<br>                 595                 600                 605 | 2124 |
| cat gag gaa ttc gcc gtc gcc gtg aag ctg atg cag ggc ggc ctc atc<br>His Glu Glu Phe Ala Val Ala Val Lys Leu Met Gln Gly Gly Leu Ile<br>        610                 615                 620 | 2172 |
| gac gtg aag ccg ctg atc acc cat act ttg ccg ctt gcc gat gcg ctt<br>Asp Val Lys Pro Leu Ile Thr His Thr Leu Pro Leu Ala Asp Ala Leu<br>625                 630                 635 | 2220 |
| cag gcc ttc gag atc gcc tcg gac aag ggg caa tcg atg aag act cag<br>Gln Ala Phe Glu Ile Ala Ser Asp Lys Gly Gln Ser Met Lys Thr Gln<br>640                 645                 650 | 2268 |
| atc gca ttc agt taaggaagag cc atg agc atc cag ctt ttc gac ctc acg<br>Ile Ala Phe Ser              Met Ser Ile Gln Leu Phe Asp Leu Thr<br>655                             660                 665 | 2319 |
| ggc aag cgc gcc ctc gtc acc ggc tcc tcg cag ggt atc ggc tat gcg<br>Gly Lys Arg Ala Leu Val Thr Gly Ser Ser Gln Gly Ile Gly Tyr Ala<br>        670                 675                 680 | 2367 |
| ctc gcc aag ggc ctt gcc gcc gcc ggc gcg gac atc gtc ctc aac ggc<br>Leu Ala Lys Gly Leu Ala Ala Ala Gly Ala Asp Ile Val Leu Asn Gly<br>685                 690                 695 | 2415 |
| cgc gac gcg gcc aag ctg gcc gcc gcg cag gaa ctc ggc gca aag<br>Arg Asp Ala Ala Lys Leu Ala Ala Ala Gln Glu Leu Gly Ala Lys<br>700                 705                 710                 715 | 2463 |
| cac acg ctc gcc ttc gac gcc acc gac cat gcc gcc gtg cgc gcg gcc<br>His Thr Leu Ala Phe Asp Ala Thr Asp His Ala Ala Val Arg Ala Ala<br>                 720                 725                 730 | 2511 |
| atc gac gcc ttc gag gcg gag gtc ggc ccc atc gac atc ctc gtc aac<br>Ile Asp Ala Phe Glu Ala Glu Val Gly Pro Ile Asp Ile Leu Val Asn<br>                 735                 740                 745 | 2559 |
| aat gcc ggc atg cag cac cgc acg ccg ctg gag gat ttc ccc gcc gat<br>Asn Ala Gly Met Gln His Arg Thr Pro Leu Glu Asp Phe Pro Ala Asp<br>        750                 755                 760 | 2607 |
| gcc ttc gag cgc atc ctg aag acc aac atc tcg acg gtc ttc aat gtc<br>Ala Phe Glu Arg Ile Leu Lys Thr Asn Ile Ser Thr Val Phe Asn Val<br>765                 770                 775 | 2655 |
| ggc cag gcc gtc gcg cgc cac atg atc gcg cgc ggc gcg ggc aag atc<br>Gly Gln Ala Val Ala Arg His Met Ile Ala Arg Gly Ala Gly Lys Ile<br>780                 785                 790                 795 | 2703 |
| atc aac atc gcc agc gtg cag acc gcg ctc gcc cgc ccc ggc atc gcg<br>Ile Asn Ile Ala Ser Val Gln Thr Ala Leu Ala Arg Pro Gly Ile Ala<br>                 800                 805                 810 | 2751 |
| ccc tat acc gcc acc aag ggc gcc gtc ggc aac ctc acc aag ggc atg<br>Pro Tyr Thr Ala Thr Lys Gly Ala Val Gly Asn Leu Thr Lys Gly Met<br>                 815                 820                 825 | 2799 |
| gcg acc gac tgg gcg aaa tac ggc ctg caa tgc aac gcc atc gcg ccg<br>Ala Thr Asp Trp Ala Lys Tyr Gly Leu Gln Cys Asn Ala Ile Ala Pro<br>        830                 835                 840 | 2847 |
| ggc tat ttc gac acg ccg ctc aat gcc gcg ctg gtc gcc gat ccg gcc<br>Gly Tyr Phe Asp Thr Pro Leu Asn Ala Ala Leu Val Ala Asp Pro Ala<br>845                 850                 855 | 2895 |
| ttt tcc gcc tgg ctg gaa aag cgc acg ccg gcc ggc cgc tgg ggc aag<br>Phe Ser Ala Trp Leu Glu Lys Arg Thr Pro Ala Gly Arg Trp Gly Lys<br>860                 865                 870                 875 | 2943 |
| gtg gag gag ctg atc ggc gcc tgc atc ttt ctt tcc tcc gac gct tcc | 2991 |

-continued

```
Val Glu Glu Leu Ile Gly Ala Cys Ile Phe Leu Ser Ser Asp Ala Ser
                880                 885                 890 tcc ttc gtg aac gga cac acg ctc tat gtc gac ggc ggc atc acg gcc      3039
Ser Phe Val Asn Gly His Thr Leu Tyr Val Asp Gly Gly Ile Thr Ala
            895                 900                 905 tcg ctc tgaggacaac aggcgcatcg tcctgatggg cgtcgccggc tgcggcaagt       3095
Ser Leu ccgccgtcgg cgcggcgctc gccgcgcggc tcggtgcgat ccccgggtac cgagctcg      3153
```

<210> SEQ ID NO 14
<211> LENGTH: 315
<212> TYPE: PRT
<213> ORGANISM: Unknown
<220> FEATURE:
<223> OTHER INFORMATION: environmental source

<400> SEQUENCE: 14

```
Met Ser Lys Ile Asp Val Leu Gln Val Gly Pro Tyr Pro Ala Trp Asp
 1               5                  10                  15

Glu Glu Arg Leu Asn Ala Thr Phe Thr Met His Arg Tyr Phe Glu Ala
                20                  25                  30

Ala Asp Lys Ala Ala Phe Leu Ala Glu His Gly Gly Thr Ile Arg Gly
            35                  40                  45

Ile Ala Thr Arg Gly Glu Leu Gly Ala Asn Arg Ala Met Ile Glu Ala
        50                  55                  60

Leu Pro Lys Leu Glu Val Ile Ser Val Tyr Gly Val Gly Phe Asp Ala
 65                  70                  75                  80

Val Asp Leu Ser Ala Ala Arg Glu Arg Gly Ile Arg Val Thr Asn Thr
                85                  90                  95

Pro Asp Val Leu Thr Lys Asp Val Ala Asp Leu Gly Ile Ala Met Met
                100                 105                 110

Leu Ala Gln Ala Arg Gly Val Ile Gly Gly Glu Ala Trp Val Lys Ser
            115                 120                 125

Gly Asp Trp Ala Ser Lys Gly Leu Tyr Pro Leu Lys Arg Arg Val His
        130                 135                 140

Gly Met Arg Ala Gly Val Leu Gly Leu Gly Arg Ile Gly Tyr Glu Val
145                 150                 155                 160

Ala Lys Arg Leu Ala Gly Phe Asp Met Asp Ile Ala Tyr Ser Asp Thr
                165                 170                 175

Gly Pro Lys Asp Phe Ala Arg Asp Trp Thr Phe Val Ala Asp Pro Ala
            180                 185                 190

Glu Leu Ala Ala Arg Ser Asp Phe Leu Phe Val Thr Leu Ala Ala Ser
        195                 200                 205

Ala Glu Thr Arg His Ile Val Gly Arg Lys Val Ile Glu Ala Leu Gly
    210                 215                 220

Pro Glu Gly Met Leu Ile Asn Ile Ser Arg Ala Ser Asn Ile Asp Glu
225                 230                 235                 240

Ser Ala Leu Leu Asp Ala Leu Glu Thr Lys Ala Leu Gly Ser Ala Ala
                245                 250                 255

Leu Asp Val Phe Glu Gly Glu Pro Asn Leu Asn Pro Arg Phe Leu Ala
            260                 265                 270

Leu Asp Asn Val Leu Leu Gln Pro His Met Ala Ser Gly Thr Ile Glu
        275                 280                 285

Thr Arg Lys Ala Met Gly Gln Leu Val Phe Asp Asn Leu Ser Ala His
    290                 295                 300
```

Phe Asp Gly Arg Pro Leu Pro Thr Pro Val Leu
305                 310             315

<210> SEQ ID NO 15
<211> LENGTH: 343
<212> TYPE: PRT
<213> ORGANISM: Unknown
<220> FEATURE:
<223> OTHER INFORMATION: environmental source

<400> SEQUENCE: 15

Met Lys Ala Ile Val Ile His Gln Ala Lys Asp Leu Arg Val Glu Asp
1               5                   10                  15

Ser Ala Val Glu Ala Pro Gly Pro Glu Val Glu Ile Arg Leu Ala
                20              25                  30

Ala Gly Gly Ile Cys Gly Ser Asp Leu His Tyr Tyr Asn His Gly Gly
            35                  40                  45

Phe Gly Thr Val Arg Leu Lys Glu Pro Met Ile Leu Gly His Glu Val
    50                  55                  60

Ser Gly His Val Ala Ala Leu Gly Glu Gly Val Ser Gly Leu Ala Ile
65              70                  75                  80

Gly Asp Leu Val Ala Val Ser Pro Ser Arg Pro Cys Gly Ala Cys Asp
                85                  90                  95

Tyr Cys Leu Lys Gly Leu Ala Asn His Cys Phe Asn Met Arg Phe Tyr
            100                 105                 110

Gly Ser Ala Met Pro Phe Pro His Ile Gln Gly Ala Phe Arg Glu Arg
        115                 120                 125

Leu Val Ala Lys Ala Ser Gln Cys Val Lys Ala Glu Gly Leu Ser Ala
    130                 135                 140

Gly Glu Ala Ala Met Ala Glu Pro Leu Ser Val Thr Leu His Ala Thr
145                 150                 155                 160

Arg Arg Ala Gly Glu Met Leu Gly Lys Arg Val Leu Val Thr Gly Cys
                165                 170                 175

Gly Pro Ile Gly Thr Leu Ser Ile Leu Ala Ala Arg Arg Ala Gly Ala
            180                 185                 190

Ala Glu Ile Val Ala Ala Asp Leu Ser Glu Arg Ala Leu Gly Phe Ala
        195                 200                 205

Arg Ala Val Gly Ala Asp Arg Thr Val Asn Leu Ser Glu Asp Arg Asp
    210                 215                 220

Gly Leu Val Pro Phe Ser Glu Asn Lys Gly Tyr Phe Asp Val Leu Tyr
225                 230                 235                 240

Glu Cys Ser Gly Ala Gln Pro Ala Leu Val Ala Gly Ile Gln Ala Leu
                245                 250                 255

Arg Pro Arg Gly Val Ile Val Gln Leu Gly Leu Gly Gly Glu Met Ser
            260                 265                 270

Leu Pro Met Met Ala Ile Thr Ala Lys Glu Leu Asp Leu Arg Gly Ser
        275                 280                 285

Phe Arg Phe His Glu Glu Phe Ala Val Ala Val Lys Leu Met Gln Gly
    290                 295                 300

Gly Leu Ile Asp Val Lys Pro Leu Ile Thr His Thr Leu Pro Leu Ala
305                 310                 315                 320

Asp Ala Leu Gln Ala Phe Glu Ile Ala Ser Asp Lys Gly Gln Ser Met
                325                 330                 335

Lys Thr Gln Ile Ala Phe Ser
            340

<210> SEQ ID NO 16
<211> LENGTH: 251
<212> TYPE: PRT
<213> ORGANISM: Unknown
<220> FEATURE:
<223> OTHER INFORMATION: environmental source

<400> SEQUENCE: 16

Met Ser Ile Gln Leu Phe Asp Leu Thr Gly Lys Arg Ala Leu Val Thr
  1               5                  10                  15

Gly Ser Ser Gln Gly Ile Gly Tyr Ala Leu Ala Lys Gly Leu Ala Ala
             20                  25                  30

Ala Gly Ala Asp Ile Val Leu Asn Gly Arg Asp Ala Ala Lys Leu Ala
         35                  40                  45

Ala Ala Ala Gln Glu Leu Gly Ala Lys His Thr Leu Ala Phe Asp Ala
     50                  55                  60

Thr Asp His Ala Ala Val Arg Ala Ala Ile Asp Ala Phe Glu Ala Glu
 65                  70                  75                  80

Val Gly Pro Ile Asp Ile Leu Val Asn Asn Ala Gly Met Gln His Arg
                 85                  90                  95

Thr Pro Leu Glu Asp Phe Pro Ala Asp Ala Phe Glu Arg Ile Leu Lys
            100                 105                 110

Thr Asn Ile Ser Thr Val Phe Asn Val Gly Gln Ala Val Ala Arg His
        115                 120                 125

Met Ile Ala Arg Gly Ala Gly Lys Ile Ile Asn Ile Ala Ser Val Gln
    130                 135                 140

Thr Ala Leu Ala Arg Pro Gly Ile Ala Pro Tyr Thr Ala Thr Lys Gly
145                 150                 155                 160

Ala Val Gly Asn Leu Thr Lys Gly Met Ala Thr Asp Trp Ala Lys Tyr
                165                 170                 175

Gly Leu Gln Cys Asn Ala Ile Ala Pro Gly Tyr Phe Asp Thr Pro Leu
            180                 185                 190

Asn Ala Ala Leu Val Ala Asp Pro Ala Phe Ser Ala Trp Leu Glu Lys
        195                 200                 205

Arg Thr Pro Ala Gly Arg Trp Gly Lys Val Glu Glu Leu Ile Gly Ala
    210                 215                 220

Cys Ile Phe Leu Ser Ser Asp Ala Ser Ser Phe Val Asn Gly His Thr
225                 230                 235                 240

Leu Tyr Val Asp Gly Gly Ile Thr Ala Ser Leu
                245                 250

<210> SEQ ID NO 17
<211> LENGTH: 32
<212> TYPE: DNA
<213> ORGANISM: Artificial Sequence
<220> FEATURE:
<223> OTHER INFORMATION: synthetic construct

<400> SEQUENCE: 17
acccaagctt caccaaaaga gtgaagagga ag                                32

<210> SEQ ID NO 18
<211> LENGTH: 34
<212> TYPE: DNA
<213> ORGANISM: Artificial Sequence
<220> FEATURE:
<223> OTHER INFORMATION: synthetic construct

<400> SEQUENCE: 18

```
cgtatctaga aaaatattct ggtgatgaag gtga                              34

<210> SEQ ID NO 19
<211> LENGTH: 34
<212> TYPE: DNA
<213> ORGANISM: Artificial Sequence
<220> FEATURE:
<223> OTHER INFORMATION: synthetic construct

<400> SEQUENCE: 19
agactctaga tccacataaa cgcactgcgt aaac                              34

<210> SEQ ID NO 20
<211> LENGTH: 33
<212> TYPE: DNA
<213> ORGANISM: Artificial Sequence
<220> FEATURE:
<223> OTHER INFORMATION: synthetic construct

<400> SEQUENCE: 20
gaggggatcc tggcttcgtg aacgatatac tgg                               33

<210> SEQ ID NO 21
<211> LENGTH: 31
<212> TYPE: DNA
<213> ORGANISM: Artificial Sequence
<220> FEATURE:
<223> OTHER INFORMATION: synthetic construct

<400> SEQUENCE: 21
aataggatcc ttcatcacca gaatattttt a                                 31

<210> SEQ ID NO 22
<211> LENGTH: 28
<212> TYPE: DNA
<213> ORGANISM: Artificial Sequence
<220> FEATURE:
<223> OTHER INFORMATION: synthetic construct

<400> SEQUENCE: 22
cataggtacc ggctttcaga taggtgcc                                     28
```

2,5-DKG PERMEASES

This application is a Divisional Application of U.S. application Ser. No. 09/922,501, which was filed Aug. 3, 2001, now U.S. Pat. No. 6,720,168 and which claims the benefit of U.S. Provisional Application Ser. No. 60/325,774, filed Aug. 4, 2000, which was converted from U.S. Ser. No. 09/633,294 and U.S. Provisional Application Ser. No. 60/42 1,141, filed Sep. 29, 2000, which was converted from U.S. Ser. No. 09/677,032, each of which is incorporated herein by reference in its entirety.

This invention was made in part with U.S. Government support under Cooperative Agreement 70NANB5H1138 and ATP NIST project Identification Number 1995-05-0007E. The U.S. Government has certain rights in this invention.

BACKGROUND OF THE INVENTION

1. Field of the Invention

The present invention relates generally to microbial transporter proteins and, more specifically, to novel 2,5-diketo-D-gluconic acid (2,5-DKG) permeases.

2. Background Information

Adequate intake of ascorbic acid, or vitamin C, is recognized as an important factor in maintaining health. To ensure adequate intake of ascorbic acid, the chemical is now added to many foods, drinks and cosmetic products, and is also sold as a direct vitamin supplement. To meet the commercial demand for ascorbic acid, there is a need to develop more efficient processes for its production.

Although there are a number of alternative methods of producing ascorbic acid, one of the least expensive and most ecologically sound methods is biofermentation. Bacterial strains have now been engineered to express all of the enzymes required for the stepwise conversion of an inexpensive sugar source, such as D-glucose, to a stable precursor of ascorbic acid, 2-keto-L-gulonic acid (2-KLG) (see U.S. Pat. No. 5,032,514 and references therein). 2-KLG can be readily converted to ascorbic acid by chemical or enzymatic procedures.

FIG. 2 shows schematically the enzymatic reactions that take place in the bioconversion of D-glucose to 2-KLG. As shown in FIG. 2, the enzymatic reactions that lead from D-glucose, to D-gluconic acid, to 2-keto-D-gluconic acid (2-KDG), to 2,5-diketo-D-gluconic acid (2,5-DKG), take place at the surface of the bacterial cell. 2,5-DKG must then enter the cell in order for its enzymatic conversion to 2-KLG.

Much effort has been expended in increasing the efficiency of the enzymatic reactions involved in 2-KLG production. For example, U.S. Pat. No. 5,032,514 describes methods for increasing 2-KLG production by reducing metabolic diversion of 2,5-DKG to products other than 2-KLG.

Increasing uptake of 2,5-DKG by a bacterial strain suitable for biofermentation could be advantageous in increasing 2-KLG production. Expressing additional copies of an endogenous 2,5-DKG permease, or expressing an exogenous 2,5-DKG permease with superior properties, could increase uptake of 2,5-DKG. However, to date, no 2,5-DKG permease has been identified or characterized that could be used in this manner.

Therefore, there exists a need to identify and characterize nucleic acid molecules encoding 2,5-DKG permeases, so that permeases with advantageous properties can be used in the commercial production of ascorbic acid and in other important applications. The present invention satisfies this need and provides related advantages as well.

SUMMARY OF THE INVENTION

The invention provides an isolated nucleic acid molecule encoding a polypeptide which has 2,5-DKG permease activity. In one embodiment, the isolated nucleic acid molecule contains a nucleotide sequence having at least 40% identity to a nucleotide sequence selected from the group consisting of SEQ ID NOS:1, 3, 5, 7, 9 and 11. In another embodiment, the isolated nucleic acid molecule contains a nucleotide sequence which encodes a polypeptide having at least 40% identity to an amino acid sequence selected from the group consisting of SEQ ID NOS:2, 4, 6, 8, 10 and 12.

Also provided are vectors and cells containing isolated nucleic acid molecules encoding polypeptides having 2,5-KDG permease activity. In one embodiment, the cells are bacterial cells selected from the genera *Pantoea* and *Klebsiella*.

The invention also provides methods of identifying and isolating nucleic acid molecules encoding polypeptides which have 2,5-DKG permease activity. Also provided are methods of enhancing 2-KLG production, by expressing the nucleic acid molecules of the invention in suitable bacterial cells.

Further provided are isolated polypeptides having 2,5-DKG permease activity, and immunogenic peptides therefrom. The invention also provides antibodies specific for such polypeptides and peptides.

BRIEF DESCRIPTION OF THE DRAWINGS

FIGS. 1A and 1B shows an alignment of the amino acid sequences of the 2,5-DKG permeases designated YiaX2 (SEQ ID NO:12); PE1 (SEQ ID NO:2); PE6 (SEQ ID NO:4); prmA (SEQ ID NO:8); prmB (SEQ ID NO:10) and PK1 (SEQ ID NO:6).

DETAILED DESCRIPTION OF THE INVENTION

Figure 2:
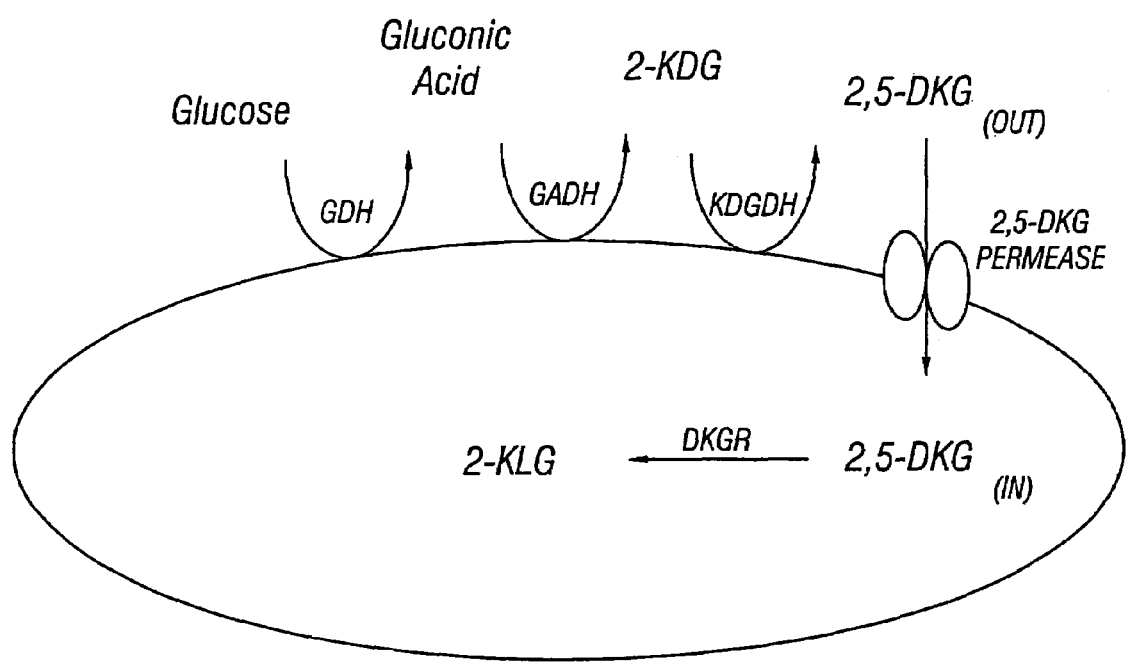
FIG. 2 shows the biosynthetic pathway from glucose to 2-KLG in a bacterial strain suitable for biofermentation.

The invention provides novel nucleic acid molecules encoding polypeptides having 2,5-DKG permease activity, and related products and methods. The molecules of the invention can advantageously be used to increase the efficiency of 2-KLG bioproduction, and thus to lower the cost of commercial ascorbic acid production.

Naturally occurring 2,5-DKG permeases are polypeptides localized to the cytoplasmic membrane of microorganisms, which are predicted, using commercially available topology prediction programs, to contain about 10 to 12 transmembrane domains. Each transmembrane spanning segment is about 20 amino acids in length, with the intracellular and extracellular loops ranging from about 2 to about 83 amino acids in length. Generally, the loop between the fifth and sixth transmembrane domain spanning segments is larger than the other loops.

Naturally occurring 2,5-DKG permeases are typically about 350–550 amino acids in length, such as about 400–450 amino acids in length, and particularly about 425–440 amino acids in length.

The nucleotide sequences encoding six exemplary 2,5-DKG permeases are set forth as follows, with the designation and organismal source of the molecule indicated in parentheses: SEQ ID NO:1 (PE1 from an environmental source); SEQ ID NO:3 (PE6 from an environmental source); SEQ ID NO:5 (PK1 from *Klebsiella oxytoca*); SEQ ID NO:7 (prmA from *Pantoea citrea*); SEQ ID NO:9 (prmB from *Pantoea citrea*); and SEQ ID NO:11 (YiaX2 from *Klebsiella oxytoca*). The corresponding encoded 2,5-DKG permease amino acid sequences are set forth as SEQ ID NO:2 (PE1); SEQ ID NO:4 (PE6); SEQ ID NO:6 (PK1); SEQ ID NO:8 (prmA); SEQ ID NO:10 (prmB); and SEQ ID NO:12 (YiaX2).

2,5-DKG permeases from different microorganisms exhibit extensive amino acid sequence relatedness over their entire length, as is evidenced by the six-way sequence alignment shown in FIG. 1. The overall identity of the six permeases shown in FIG. 1 is about 17%, and the overall similarity, taking into account conservative substitutions, is about 43%.

Based on their predicted topological and sequence similarity, 2,5-DKG permeases disclosed herein can be further subdivided into two structural families. The three 2,5-DKG permeases designated YiaX2, PE6 and PrmA are representative of one family of permeases, sharing about 50% overall identity in a three-way amino acid sequence alignment. The three 2,5-DKG permeases designated PK1, PE1 and PrmB are representative of a second family of related permeases, sharing about 60% overall identity in a three-way amino acid sequence alignment.

Naturally occurring 2,5-DKG permeases also exhibit 2,5-DKG permease activity. The term "2,5-DKG permease activity," as used herein, refers to the ability of the polypeptide, when expressed in its native orientation at the cell membrane, to transport 2,5-DKG across the cytoplasmic membrane, in comparison with an unrelated control polypeptide. Such transport can be either unidirectional or bidirectional.

2,5-DKG permease activity can be determined by a variety of methods. For example, 2,5-DKG permease activity can be determined using a metabolic selection assay, as described further in the Example, below. Briefly, a bacterial cell either naturally deficient in 2,5-DKG permease activity, or made deficient in 2,5-DKG permease activity, is identified or produced. As described in the Example, bacterial cells can be made deficient in endogenous 2,5-DKG permease activity by preparing a deletion mutant of one or more endogenous 2,5-DKG permease genes, using the polymerase chain reaction, following methods known in the art. The term "deficient," as used in relation to a cell deficient in 2,5-DKG-permease activity, is intended to refer to endogenous 2,5-DKG permease activity that is comparable to, or less than, the endogenous permease activity of a *K. oxytoca* strain deleted in the yiaX2 gene, such as the strain *K. oxytoca* ΔyiaX2 [tkr idnO], as assessed either by a growth assay or by a 2,5-DKG uptake assay.

A cell useful in a metabolic selection assay to determine 2,5-DKG permease activity of an expressed polypeptide can further naturally be capable of converting intracellular 2,5-DKG to carbon and energy, or made capable of such conversion by recombinant expression of appropriate metabolic enzymes. As described in the Example, a combination of nucleic acid molecules encoding a 2-keto-reductase (tkr) and a 5-keto-reductase (idnO), from any bacterial species, can be expressed in the cell, which together provide the cell with the ability to catalyze the reduction of 2,5-DKG to gluconic acid. Gluconic acid can then be used by the cell as a carbon and energy source that supports cell growth.

Figure 3:
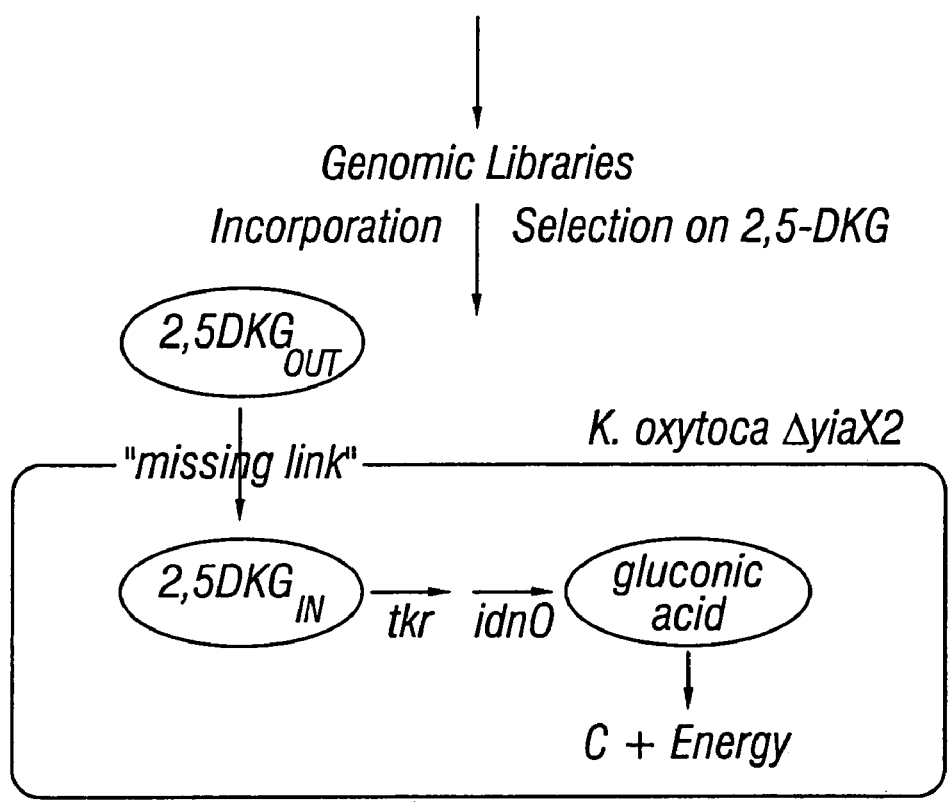
FIG. 3 shows the metabolic selection strategy used to identify novel 2,5-DKG permeases.

An exemplary bacterial cell suitable for metabolic assays to determine 2,5-DKG permease activity is the strain *K. oxytoca* ΔyiaX2 [tkr idnO] shown in FIG. 3 and described in the Example, below. This strain has a deleted yiaX2 2,5-DKG permease gene, and also recombinantly expresses the tkr/idnD/idnO operon set forth as SEQ ID NO:13 on a high copy number plasmid. Within SEQ ID NO:13, nucleotides 292–1236 encode a 2-keto-reductase (tkr) (SEQ ID NO:14); nucleotides 1252–2280 encode an idonic acid dehydrogenase (idnD) (SEQ ID NO:15); and nucleotides 2293–3045 encode a 5-keto-reductase (idnO) (SEQ ID NO:16). Alternatively, nucleic acid molecules encoding polypeptides which contain modifications from the amino acid sequences designated SEQ ID NO:14 or 16, but which retain 2-keto-reductase activity or 5-keto-reductase activity, respectively, can be used in metabolic assays. Exemplary amino acid sequences have at least 60%, such as at least 70%, preferably 80%, 90%, 95% or greater identity to SEQ ID NOS:14 or 16, respectively.

The ability of such a bacterial cell to grow on medium containing 2,5-DKG as the sole carbon source, upon expression of a candidate 2,5-DKG permease, is a measure of the ability of the expressed permease to transport 2,5-DKG into the cell, and is thus a measure of its 2,5-DKG permease activity. Each of SEQ ID NOS:2, 4, 6, 8, 10 and 12 was demonstrated to have 2,5-DKG permease activity, as evidenced by the ability of *K. oxytoca* ΔyiaX2 [tkr idno] expressing each permease to grow on 2,5-DKG as the sole carbon source.

Likewise, 2,5-DKG permease activity can be determined by measuring uptake of labeled or unlabeled 2,5-DKG. For example, 2,5-DKG can be detectably labeled, such as with a fluorescent or radioactive tag. The ability of a cell or membrane vesicle expressing a 2,5-DKG permease to take up the detectable label when provided with detectably labeled 2,5-DKG, can be determined using detection assays specific for the particular label, which are well known in the art. Likewise, uptake of unlabeled 2,5-DKG can be measured by HPLC or other sensitive detection assay known in the art. Uptake of 2,5-DKG is thus a measure of permease activity. Each of SEQ ID NOS:2, 4, 6, 8, 10 and 12 exhibits 2,5-DKG permease activity as determined by assay of uptake of radiolabeled 2,5-DKG by bacterial cells expressing the recombinant permeases.

Additionally, 2,5-DKG permease activity can be measured in any cell in which 2,5-DKG can be converted to a product, by measuring production of the product in the presence of extracellular 2,5-DKG. For example, in a cell naturally expressing, or recombinantly expressing, a 2,5-DKG reductase, intracellular 2,5-DKG is converted to 2-KLG. The ability of the bacterial cell to produce 2-KLG when provided with extracellular 2,5-DKG, upon expression of a 2,5-DKG permease, is a measure of the ability of the expressed permease to transport 2,5-DKG into the cell, and is thus a measure of its 2,5-DKG permease activity. Intracellular 2-KLG can be detected, for example, using HPLC or other sensitive detection methods known in the art. Other metabolic products of 2,5-DKG can also be detected, by similar methods.

It will be appreciated that a variety of alternative assays can be used to determine 2,5-DKG permease activity. For instance, the change in pH across a cell or vesicle membrane as 2,5-DKG, an acid, is transported across the membrane can be detected. Similarly, a decrease over time in extracellular 2,5-DKG can be determined.

Accordingly, using any of the activity assays described herein, those skilled in the art can distinguish between a polypeptide having 2,5-DKG permease activity, and a polypeptide not having such activity.

A 2,5-DKG permease of the invention can selectively transport 2,5-DKG. As used herein in relation to transport activity, the term "selective" refers to preferential transport of 2,5-DKG rather than 2-KLG into or out of the cell. A permease that selectively transports 2,5-DKG will transport 2,5-DKG at least 2-fold, such as at least 5-fold, including greater than 10-fold more efficiently than it transports 2-KLG. A permease that selectively transports 2,5-DKG is particularly advantageous in applications where it is desirable to increase intracellular production of 2-KLG, such as in the commercial production of ascorbic acid. In particular, employing a permease that selectively transports 2,5-DKG prevents intracellular 2-KLG from competing with extracellular 2,5-DKG for permease-mediated transport through the membrane, and increases the overall efficiency of intracellular 2-KLG production.

It will be appreciated that the assays described above for determining 2,5-DKG permease activity can be modified to simultaneously, or separately, determine 2-KLG permease activity. For example, a metabolic assay can be designed in which a bacterial cell can convert either intracellular 2,5-DKG or 2-KLG to carbon and energy. In such a cell, the relative ability of the cell to grow on 2,5-DKG as the sole carbon source, compared with its ability to grow on 2-KLG as the sole carbon source, is a measure of the ability of the expressed permease to selectively transport 2,5-DKG. Using such an assay, it was determined that the 2,5-DKG permeases designated YiaX2, PE1, PE6, prmA and prmB are non-selective for 2,5-DKG, as they also efficiently catalyze the transport of 2-KLG, as *K. oxytoca* ΔyiaX2 [tkr idnO] cells expressing such permeases grow well on either 2,5-DKG or 2-KLG. In contrast, PK1 selectively transports 2,5-DKG, and *K. oxytoca* ΔyiaX2 [tkr idnO] cells expressing PK1 (SEQ ID NO:6) grow on 2,5-DKG but not on 2-KLG as the sole carbon source.

The invention provides an isolated nucleic acid molecule encoding a polypeptide which has 2,5-DKG permease activity. The invention nucleic acid molecules of the invention are suitable for a variety of commercial and research applications. For example, one or more of the invention nucleic acid molecules can be expressed in bacterial cells in order to enhance the rate of uptake of 2,5-DKG by the cells. Enhancing uptake of 2,5-DKG has a variety of applications, such as in commercial production of 2,5-DKG itself, or commercial production of any metabolic product of 2,5-DKG. For example, 2,5-DKG uptake is a rate limiting step in the biosynthesis of 2-KLG, which is a stable intermediate in the synthesis of ascorbic acid. 2-KLG can thus be obtained from bacterial cells expressing 2,5-DKG permeases, and converted to ascorbic acid.

Additionally, the invention nucleic acid molecules can be used as probes or primers to identify and isolate 2,5-DKG permease homologs from additional species, or as templates for the production of mutant permeases, using methods known in the art and described further below. Such permeases can have advantageous properties compared with the 2,5-DKG permeases disclosed herein as SEQ ID NOS:2, 4, 6, 8, 10 and 12, such as greater enzymatic activity or greater 2,5-DKG selectivity.

In one embodiment, an isolated nucleic acid molecule of the invention is not completely contained within the nucleotide sequence designated SEQ ID NO:19 of WO 00/22170, which is the *K. oxytoca* yia operon. In another embodiment, the isolated nucleic acid molecule of the invention is not completely contained within the nucleotide sequence herein designated SEQ ID NO:11. In another embodiment, the encoded polypeptide is not completely contained within the amino acid sequence herein designated SEQ ID NO:12.

The term "isolated," as used herein, is intended to mean that the molecule is altered, by the hand of man, from how it is found in its natural environment. For example, an isolated nucleic acid molecule can be a molecule operatively linked to an exogenous nucleic acid sequence. An isolated nucleic acid molecule can also be a molecule removed from some or all of its normal flanking nucleic acid sequences, such as removed from one or more other genes within the operon in which the nucleic acid molecule is normally found.

Specifically with respect to an isolated nucleic acid molecule containing the nucleotide sequence designated SEQ ID NO:11, or encoding the yiaX2 polypeptide designated SEQ ID NO:12, the term "isolated" is intended to mean that the nucleic acid molecule does not contain any of the flanking open reading frames (orfs) present in the *K. oxytoca* yia operon, such as the orfs designated lyxK and orf1, described in WO 00/22170.

An isolated molecule can alternatively, or additionally, be a "substantially pure" molecule, in that the molecule is at least 60%, 70%, 80%, 90 or 95% free from cellular components with which it is naturally associated. An isolated nucleic acid molecule can be in any form, such as in a buffered solution, a suspension, a heterologous cell, a lyophilized powder, or attached to a solid support.

The term "nucleic acid molecule" as used herein refers to a polynucleotide of natural or synthetic origin. A nucleic acid molecule can be single- or double-stranded genomic DNA, cDNA or RNA, and represent either the sense or antisense strand or both. A nucleic acid molecule can thus correspond to the recited sequence, to its complement, or both.

The term "nucleic acid molecule" is intended to include nucleic acid molecules that contain one or more non-natural nucleotides, such as nucleotides having modifications to the base, the sugar, or the phosphate portion, or having one or more non-natural linkages, such as phosphothioate linkages. Such modifications can be advantageous in increasing the stability of the nucleic acid molecule, particularly when used in hybridization applications.

Furthermore, the term "nucleic acid molecule" is intended to include nucleic acid molecules modified to contain a detectable moiety, such as a radiolabel, a fluorochrome, a ferromagnetic substance, a luminescent tag or a detectable binding agent such as biotin. Nucleic acid molecules containing such moieties are useful as probes for detecting the presence or expression of a 2,5-DKG permease nucleic acid molecule.

In one embodiment, the isolated nucleic acid molecule encoding a polypeptide which has 2,5-DKG permease activity contains a nucleotide sequence comprising nucleotides 1–20, 1–100, 101–120, 101–200, 201–220, 201–300, 301–320, 301–400, 401–420, 401–500, 501–520, 501–600, 601–620, 601–700, 701–720, 701–800, 801–820, 801–900, 901–920, 901–1000, 1001–1020, 1001–1100, 1101–1120, 1100–1200, 1201–1220, 1201–1300, 1301–1320, 1301–1400, 1401–1420 or 1401–1500 of any of SEQ ID NOS:1, 3, 5, 7, 9 or 11.

In another embodiment, the isolated nucleic acid molecule encoding a polypeptide which has 2,5-DKG permease activity encodes an amino acid sequence comprising amino acids 1–10, 1–50, 51–60, 51–100, 101–110, 101–150, 151–160, 151–200, 201–210, 201–250, 251–260, 251–300, 301–310, 301–350, 351–361, 351–400, 401–410 or 401–439 of any of SEQ ID NOS:2, 4, 6, 8, 10 or 12.

In one embodiment, the isolated nucleic acid molecule encoding a polypeptide which has 2,5-DKG permease activity contains a nucleotide sequence having at least 35% identity to any of the 2,5-DKG permease nucleic acid molecules designated SEQ ID NOS:1, 3, 5, 7, 9 or 11. Preferably, such a molecule will have at least 40% identity to any of these recited SEQ ID NOS, such as at least 45%, 50%, 60%, 70% or 80% identity, including at least 90%, 95%, 98%, 99% or greater identity to SEQ ID NOS:1, 3, 5, 7, 9 or 11.

In another embodiment, the isolated nucleic acid molecule encoding a polypeptide which has 2,5-DKG permease activity contains a nucleotide sequence which encodes a polypeptide having at least 35% identity to any of the 2,5-DKG permease polypeptides designated SEQ ID NOS: 2, 4, 6, 8, 10 or 12. Preferably, the encoded polypeptide will have at least 40% identity to any of these recited SEQ ID NOS, such as at least 45%, 50%, 60%, 70%, 80% identity, including at least 90%, 95%, 98%, 99% or greater identity to SEQ ID NOS:2, 4, 6, 8, 10 or 12.

The term "percent identity" with respect to a nucleic acid molecule or polypeptide of the invention is intended to refer to the number of identical nucleotide or amino acid residues between the aligned portions of two sequences, expressed as a percent of the total number of aligned residues, as determined by comparing the entire sequences using a CLUSTAL V computer alignment and default parameters. CLUSTAL V alignments are described in Higgens, *Methods Mol. Biol.* 25:307–318 (1994), and an exemplary CLUSTAL V alignment of 2,5-DKG permease amino acid sequences is presented in FIG. 1.

Due to the degeneracy of the genetic code, the nucleotide sequence of a native nucleic acid molecule can be modified and still encode an identical or substantially similar polypeptide. Thus, degenerate variants of SEQ ID NOS:1, 3, 5, 7, 9 or 11 are exemplary invention nucleic acid molecules encoding polypeptides having 2,5-DKG permease activity.

Additionally, nucleic acid molecules encoding 2,5-DKG permeases from other species of microorganisms are exemplary invention nucleic acid molecules. The six permeases designated YiaX2, PE1, PE6, prmA, prmB and PK1, which were isolated from at least three, and likely four, different species of microorganisms, share substantial nucleotide sequence identity. For example, the two most similar of the disclosed 2,5-DKG permease nucleotide sequences, SEQ ID NO:5 (PK1) and SEQ ID NO:1 (PE1), share 86% identity across their length. The two most dissimilar of the disclosed 2,5-DKG permease nucleotide sequences, SEQ ID NO:7 (prmA) and SEQ ID NO:9 (prmB), share 51% identity across their length. In contrast, a search of GenBank reveals no other nucleotide sequences, including sequences which encode transporter proteins and other transmembrane proteins, that exhibit significant identity or similarity to any of the disclosed 2,5-DKG permease nucleotide sequences over the entire length of their sequences.

The six permeases disclosed herein also share substantial amino acid sequence identity over their entire length, as described previously. For example, PK1 from *Klebsiella oxytoca* (SEQ ID NO:6), and PE1, from an environmental source (SEQ ID NO:2), are 93% identical at the amino acid level. The amino acid sequence in the GenBank database most closely related to a 2,5-DKG permease, which is a putative tartrate transporter from *Agrobacterium vitis* (GenBank Accession U32375 or U25634) is 33% identical to SEQ ID NO:12 (YiaX2), and shares less identity with the other disclosed 2,5-DKG permeases. Other sequences with some degree of identity in the GenBank database to the disclosed 2,5-DKG permease include membrane transporter proteins from a variety of species, including phthalate transporter proteins from *B. cepacia* (AF152094) and *P. putida* (D13229); hydroxyphenylacetate transporters from *S. dublin* (AF144422) and *E. coli* (Z37980); and probable transporter proteins from *S. coelicolor* (AL136503 and AL132991) each of which has about 27% or less identity at the amino acid level to the recited SEQ ID NOS.

In view of the high degree of identity between different 2,5-DKG permease nucleic acid molecules and encoded polypeptides within a single species and between different microbial species, additional 2,5-DKG permeases from other species can be readily identified and tested. Thus, nucleic acid molecules of the invention include nucleic acid molecules that encode polypeptides having 2,5-DKG permease activity from any microbial species. Microorganisms that contain 2,5-DKG permeases can be recognized by their ability to actively transport 2,5-DKG, such that they can grow on 2,5-DKG as the sole carbon source, or incorporate 2,5-DKG in an uptake assay. Such microorganisms can include, for example, bacteria, including Archaebacteria, gram positive and gram negative bacteria; yeast; and fungi.

Exemplary bacteria which contain 2,5-DKG permeases include Proteobacteria, and more specifically Enterobacteria and *Pseudomonads* (e.g. *P. aeruginosa*), as described in the Example. Exemplary *Enterobacteria* include species from the genera *Klebsiella* (e.g. *K. oxytoca*, from which SEQ ID NOS:5 and 11 were obtained) and *Pantoea* (e.g. *P. citrea*, from which SEQ ID NOS:7 and 9 were obtained, and *P. agglomerans*). Sources of such microorganisms include public repositories, such as the American Type Culture Collection (ATCC), and commercial sources. It will be appreciated that the taxonomy and nomenclature of bacterial genera are such that the same or similar strains are sometimes reported in the literature as having different names. For example, *Klebsiella oxytoca* (e.g. ATCC 13182) has alternatively been described as *Aerobacter aerogenes, Klebsiella aerogenes* and *Klebsiella pneumoniae*. Likewise, *Pantoea agglomerans* (e.g. ATCC 21998) has alternatively been described as *Erwinia herbicola* and *Acetomonas albosesamae*. The terms "*Klebsiella*" and "*Pantoea*," as used herein, are intended to refer to the genera of the strains deposited as ATCC 13182 and 21998, respectively.

Additionally, microorganisms from which 2,5-DKG permease nucleic acid molecules can be obtained are microorganisms present in environmental samples. For example, the 2,5-DKG permease nucleic acid molecules designated SEQ ID NOS:1 and 3 were obtained from environmental samples. As used herein, the term "environmental sample" refers to a sample obtained from natural or man-made environments, which generally contains a mixture of microorganisms.

Exemplary environmental samples are samples of soil, sand, freshwater or freshwater sediments, marine water or marine water sediments, industrial effluents, hot springs, thermal vents, and the like. Within an environmental sample there are likely to be microorganisms that are unidentified, and also microorganisms that are uncultivable. Isolation of invention 2,5-DKG permease molecules of the invention from microorganisms present in environmental samples does not require either identification or culturing of the microorganism.

Furthermore, nucleic acid molecules of the invention include nucleic acid molecules encoding amino acid sequences that are modified by one or more amino acid additions, deletions or substitutions with respect to the native sequence of SEQ ID NOS:2, 4, 6, 8, 10 or 12. Such modifications can be advantageous, for example, in enhancing the stability, expression level, enzymatic activity, or 2,5-DKG selectivity of the permease. If desired, such modifications can be randomly generated, such as by chemical mutagenesis, or directed, such as by site-directed mutagenesis of a native permease sequence, using methods well known in the art.

An amino acid sequence that is modified from a native permease amino acid sequence can include one or more conservative amino acid substitutions, such as substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); or substitution of an uncharged polar amino acid with another uncharged polar amino acid (such as replacement of a serine with a glycine, threonine, tyrosine, cysteine, asparagine or glutamine). A modified amino acid sequence can also include one or more nonconservative substitutions without adversely affecting the desired biological activity.

Computer programs known in the art can provide guidance in determining which amino acid residues can be substituted without abolishing the enzymatic activity of a 2,5-DKG permease (see, for example, Eroshkin et al., *Comput. Appl. Biosci.* 9:491–497 (1993)).

Additionally, guidance in modifying amino acid sequences while retaining or enhancing functional activity is provided by aligning homologous 2,5-DKG permease polypeptides from various species (see FIG. 1). It is well known in the art that evolutionarily conserved amino acid residues and domains are more likely to be important for maintaining biological activity than less well-conserved residues and domains. Thus, it would be expected that substituting a residue which is highly conserved among the six 2,5-DKG permeases shown in FIG. 1 (or among the members of the two structural families of permeases, defined as SEQ ID NOS:2, 6 and 10, and SEQ ID NOS:4, 8 and 12) with a non-conserved residue may be deleterious, whereas making the same substitution at a residue which varies widely among the different permeases would likely not have a significant effect on biological activity.

A comparison of the amino acid sequences of PE1 (SEQ ID NO:2), which transports both 2,5-DKG and 2-KLG, and PK1 (SEQ ID NO:6), which selectively transports 2,5-DKG, indicates that the regions responsible for 2,5-DKG selectivity must reside in the 7% of amino acids which differ between these two sequences. Therefore, modifying all or some of these differing residues in a 2,5-DKG permease to those found in the PK1 sequence would be expected to increase 2,5-DKG selectivity of the permease.

Alignment of the six 2,5-DKG permeases described herein also provides guidance as to regions where additions and deletions are likely to be tolerated. For example the N and C termini, and the region around amino acids 225–250 (based on the numbering of SEQ ID NO:12 (yiaX2)) appear to be regions that are relatively tolerant of amino acid insertions and deletions, as evidenced by gaps in the sequence alignment. Modified 2,5-DKG permeases can thus include "tag" sequences at such sites, such as epitope tags, histidine tags, glutathione-S-transferase (GST) and the like, or sorting sequences. Such additional sequences can be used, for example, to facilitate purification or characterization of a recombinant 2,5-DKG permease.

It will be appreciated that confirmation that any particular nucleic acid molecule is a nucleic acid molecule of the invention can be obtained by determining the 2,5-DKG permease activity of the encoded polypeptide, using one or more of the functional assays described herein.

The invention further provides an isolated nucleic acid molecule encoding a polypeptide which has 2,5-DKG permease activity, wherein the nucleic acid molecule is operatively linked to a promoter of gene expression. The term "operatively linked," as used herein, is intended to mean that the nucleic acid molecule is positioned with respect to either the endogenous promoter, or a heterologous promoter, in such a manner that the promoter will direct the transcription of RNA using the nucleic acid molecule as a template.

Methods for operatively linking a nucleic acid to a desired promoter are well known in the art and include, for example, cloning the nucleic acid into a vector containing the desired promoter, or appending the promoter to a nucleic acid sequence using PCR. A nucleic acid molecule operatively linked to a promoter of RNA transcription can be used to express 2,5-DKG transcripts and polypeptides in a desired host cell or in vitro transcription-translation system.

The choice of promoter to operatively link to an invention nucleic acid molecule will depend on the intended application, and can be determined by those skilled in the art. For example, if a particular gene product may be detrimental to a particular host cell, it may be desirable to link the invention nucleic acid molecule to a regulated promoter, such that gene expression can be turned on or off. An exemplary inducible promoter known in the art is the lacPO promoter/operator, which is repressed by the $lacI^q$ gene product provided by certain host cells, and induced in the presence of 0.01 to 1 mM IPTG (see Example, below). For other applications, weak or strong constitutive promoters may be preferred.

The invention further provides a vector containing an isolated nucleic acid molecule encoding a polypeptide which has 2,5-DKG permease activity. The vectors of the invention will generally contain elements such as a bacterial origin of replication, one or more selectable markers, and one or more multiple cloning sites. The choice of particular elements to include in a vector will depend on factors such as the intended host cell or cells; whether expression of the inserted sequence is desired; the desired copy number of the vector; the desired selection system, and the like. The factors involved in ensuring compatibility between a host and a vector for different applications are well known in the art.

In applications in which the vectors will be used for recombinant expression of the encoded polypeptide, the isolated nucleic acid molecules will generally be operatively linked to a promoter of gene expression, as described above, which may be present in the vector or in the inserted nucleic acid molecule. In cloning and subcloning applications, however, promoter elements need not be present.

An exemplary vector suitable for both cloning applications and for expressing 2,5-DKG permeases in different bacterial species is the low copy number plasmid pCL1920 described by Lerner et al., *Nucleic Acids Res.* 18:4621 (1994), which contains a spectinomycin resistance gene (see Example, below).

Also provided are cells containing an isolated nucleic acid molecule encoding a polypeptide which has 2,5-DKG permease activity. The isolated nucleic acid molecule will generally be contained within a vector compatible with replication in the particular host cell. However, for certain applications, incorporation of the nucleic acid molecule into the bacterial genome will be preferable.

The cells of the invention can be any cells in which a 2,5-DKG permease will be expressed and folded into an active conformation. Guidance in choosing appropriate host cells is provided by identifying cell types which express other functional 10 to 12 transmembrane transporter proteins. For example, 10 to 12 transmembrane transporter proteins are found in a variety of bacterial species, as well as in yeast (e.g. *S. pombe*), *Arabidopsis*, and *Drosophila*. Therefore, depending on the particular application for the host cell, a host cell of the invention can be a bacterial cell, yeast, *Arabidopsis* or *Drosophila* cell.

In a preferred embodiment, the cell is a bacterial cell. The choice of bacterial cell will depend on the intended application. For example, for routine subcloning applications, the cell can be any convenient laboratory strain of bacteria, such as *E. coli*, which can be transformed with the isolated nucleic acid molecules and vectors of the invention by methods well known in the art.

For assessment of encoded 2,5-DKG permease activity, the cell can be a bacterial strain suitable for metabolic assays, such as a strain which endogenously expresses, or which is engineered to express, enzymes that catalyze the conversion of 2,5-DKG to essential products. An exemplary strain suitable for metabolic assays is the *K. oxytoca* ΔyiaX2 [tkr idnO] strain designated MGK002 [pDF33] described further in the Example, below, which provides for the conversion of intracellular 2,5-DKG to gluconic acid, which can be used as a carbon and energy source.

For use in the commercial bioproduction of 2,5-DKG metabolites, the cell can be a bacterial strain which endogenously expresses, or which is engineered to express, a 2,5-DKG reductase. As described in U.S. Pat. No. 5,032,514, 2,5-DKG reductases are found in genera including *Brevibacterium, Arthrobacter, Micrococcus, Staphylococcus, Pseudomonas, Bacillus, Citrobacter* and *Corynebacterium*. Therefore, a cell of the invention can be a bacterial cell of any of these genera, or a bacterial cell engineered to express a 2,5-DKG reductase of any of these genera.

A cell able to produce 2,5-DKG metabolites will preferably also be able to catalyze the extracellular production of 2,5-DKG from an inexpensive carbon source, such as glucose. An exemplary pathway from D-glucose to 2,5-DKG involves the enzymatic conversion of D-glucose to D-gluconic acid (catalyzed by D-glucose dehydrogenase), from D-gluconic acid to 2-Keto-D-gluconic acid (catalyzed by D-gluconate dehydrogenase), and from 2-Keto-D-gluconic acid to 2,5-DKG (catalyzed by 2-Keto-D-gluconic acid dehydrogenase), as is shown in FIG. 2. These steps can be carried out by organisms of several genera, including Gluconobacter, Acetobacter and *Erwinia* (also called *Pantoea*).

A bacterial cell useful for the production of 2-KLG from D-glucose is the *Pantoea aggolmerans* (also referred to as *Erwinia herbicola* or *Acetomonas albosesamae*) strain described in U.S. Pat. No. 5,032,514, designated ATCC 21998 ptrp 1–35 tkrAΔ3, or a derivative of this strain with improved properties. Contemplated improvements to this strain, which can be produced by genetic engineering, include deletion of enzymes that divert glucose to metabolites other than 2-KLG, such that yield of 2-KLG is increased. Other contemplated improvements to this strain include mutations that provide for improved recovery and purification of 2-KLG.

The *Pantoea* strain described in U.S. Pat. No. 5,032,514 recombinantly expresses a 2,5-DKG reductase from *Corynebacterium* (described in U.S. Pat. No. 4,757,012). The strain further contains a mutation that results in a non-functional tkrA gene and is thus deficient in 2-keto reductase activity. Mutation of the tkrA gene is advantageous in reducing metabolic diversion of 2-KLG to L-idonic acid, and metabolic diversion of 2,5-DKG to 5-keto-D-gluconate from 2-KLG.

Expression of one or more 2,5-DKG permeases of the invention in such cells significantly increases overall production of 2-KLG from D-glucose, which lowers the cost of commercial production of ascorbic acid.

The cells of the invention can contain one, two or more isolated nucleic acid molecules of the invention that encode polypeptides having 2,5-DKG permease activity. For example, the cell can contain an isolated nucleic acid molecule encoding at least one polypeptide having at least 80% identity to any of SEQ ID NOS:2, 4, 6, 8, 10 or 12, and optionally will contain two or more such nucleic acid molecules, in any combination. Preferably, at least one such encoded polypeptide selectively transports 2,5-DKG.

In a preferred embodiment, a bacterial cell of the invention suitable for bioproduction of 2-KLG contains an isolated nucleic acid molecule encoding a polypeptide having at least 95% identity to the 2,5-DKG selective permease designated SEQ ID NO:8 (prmA); and optionally further containing at least one isolated nucleic acid molecule encoding a polypeptide having at least 95%. identity to a 2,5-DKG permease selected from the group consisting of SEQ ID NO:4 (PE6), SEQ ID NO:10 (prmB) and SEQ ID NO:6 (PK1).

The invention also provides a method of enhancing production of 2-KLG. The method consists of culturing a bacterial cell, wherein the cell contains an isolated nucleic acid molecule encoding a polypeptide which has 2,5-DKG permease activity, under conditions wherein the encoded 2,5-DKG permease is expressed and intracellular 2,5-DKG is converted to 2-KLG. Cells suitable for this purpose, such as the Pantoea strain described in U.S. Pat. No. 5,032,514, have been described above. Optionally, the 2-KLG so produced can be chemically or enzymatically converted to a desired product such as ascorbic acid, following methods known in the art.

The invention further provides isolated oligonucleotide molecules that contain at least 17 contiguous nucleotides from any of the nucleotide sequences referenced as SEQ ID NOS:1, 3, 5, 7, 9 or 11. As used herein, the term "oligonucleotide" refers to a nucleic acid molecule that contains at least 17 contiguous nucleotides from the reference sequence and which may, but need not, encode a functional protein. Thus, an oligonucleotide of the invention can contain at least 18, 19, 20, 22 or 25 contiguous nucleotides, such as at least 30, 40, 50, 60, 70, 80, 90, 100, 125, 150, 175, 200, 250, 300, 400, 500, 750, 1000 or more contiguous nucleotides from the reference nucleotide sequence, up to the full length of the reference nucleotide sequence. The oligonucleotides of the invention are thus of sufficient length to be useful as sequencing primers, PCR primers, hybridization probes or antisense reagents, and can also encode polypeptides having 2,5-DKG permease activity, or immunogenic peptides therefrom. Those skilled in the art can determine the appropriate length and sequence of an oligonucleotide of the invention for a particular application.

For certain applications, such as for detecting 2,5-DKG expression in a cell or library, it will be desirable to use isolated oligonucleotide molecules of the invention that specifically hybridize to a nucleic acid molecule encoding a 2,5-DKG permease. The term "specifically hybridize" refers to the ability of a nucleic acid molecule to hybridize, under stringent hybridization conditions as described below, to a nucleic acid molecule that encodes a 2,5-DKG permease, without hybridizing to a substantial extent under the same conditions with nucleic acid molecules that do not encode 2,5-DKG permeases, such as unrelated molecules that fortuitously contain short regions of identity with a permease sequence. Thus, a nucleic acid molecule that "specifically hybridizes" is of a sufficient length and contains sufficient distinguishing sequence from a 2,5-DKG permease to be characteristic of the 2,5-DKG permease. Such a molecule will generally hybridize, under stringent conditions, as a single band on a Northern blot or Southern blot prepared from mRNA of a single species.

As used herein, the term "stringent conditions" refers to conditions equivalent to hybridization of a filter-bound nucleic acid molecule to a nucleic acid in a solution containing 50% formamide, 5× Denhart's solution, 5×SSPE, 0.2% SDS at 42° C., followed by washing the filter in 0.1×SSPE, and 0.1% SDS at 65° C. twice for 30 minutes. Equivalent conditions to the stringent conditions set forth above are well known in the art, and are described, for example in Sambrook et al., *Molecular Cloning: A Laboratory Manual*, Cold Spring Harbor Laboratory, New York (1992).

Nucleotide sequences that are characteristic of each of SEQ ID NOS:1, 3, 5, 7 or 9, or which are common to two, three or more of SEQ ID NOS:1, 3, 5, 7, 9 or 11 can readily be determined by aligning the sequences using a CLUSTAL V alignment program. Oligonucleotides containing regions which are common to two or more different 2,5-DKG permease nucleic acid molecules can advantageously be used as PCR primers or hybridization probes to isolate or detect nucleic acid molecules encoding 2,5-DKG permeases from other species.

The oligonucleotides of the invention can, but need not, encode polypeptides having 2,5-DKG activity. Thus, the invention oligonucleotides can contain sequences from the 5' or 3' untranslated region, or both, of the nucleotide sequences designated SEQ ID NOS:1, 3, 5, 7, 9 or 11, or contain coding sequences, or both. As described above with respect to the term "nucleic acid molecule," the invention oligonucleotides can be derived from either the sense or antisense strand of the recited SEQ ID NO.

The oligonucleotides of the invention can also advantageously be used to direct the incorporation of amino acid additions, deletions or substitutions into a recombinant 2,5-DKG permease. In such applications, it will be understood that the invention oligonucleotides can contain nucleotide modifications with respect to SEQ ID NOS:1, 3, 5, 7, 9 or 11 such that the oligonucleotides encode the desired amino acid modifications to SEQ ID NOS:2, 4, 6, 8, 10 or 12, so long as they contain at least 17 contiguous residues from the reference sequence.

Exemplary oligonucleotides of the invention are oligonucleotides that contain a sequence selected from nucleotides 1–20, 1–100, 101–120, 101–200, 201–220, 201–300, 301–320, 301–400, 401–420, 401–500, 501–520, 501–600, 601–620, 601–700, 701–720, 701–800, 801–820, 801–900, 901–920, 901–1000, 1001–1020, 1001–1100, 1101–1120, 1100–1200, 1201–1220, 1201–1300, 1301–1320, 1301–1400, 1401–1420 or 1401–1500 of any of SEQ ID NOS:1, 3, 5, 7, 9 or 11.

The invention further provides a kit containing a pair of 2,5-DKG permease oligonucleotides packaged together, either in a single container or separate containers. The pair of oligonucleotides are preferably suitable for use in PCR applications for detecting or amplifying a nucleic acid molecule encoding a 2,5-DKG permease. The kit can further contain written instructions for use of the primer pair in PCR applications, or solutions and buffers suitable for such applications.

The invention further provides isolated oligonucleotides that contain a nucleotide sequence encoding a peptide having at least 10 contiguous amino acids of an amino acid selected from the group consisting of SEQ ID NOS:2, 4, 6, 8, 10 or 12. Such oligonucleotides can encode at least 10, 12, 15, 20, 25 or more contiguous amino acids of SEQ ID NOS:2, 4, 6, 8, 10 or 12, such as at least 30, 40, 50, 75, 100, 200, 300, 400 or more contiguous amino acids from the reference sequence. The encoded peptides can be expressed from such oligonucleotides, by routine methods, and used to produce, purify or characterize 2,5-DKG antibodies, as will be discussed further below. The peptides encoded by such oligonucleotides can, but need not, additionally have 2,5-DKG permease enzymatic activity.

In one embodiment, the isolated oligonucleotide encodes an amino acid sequence selected from amino acids 1–10, 1–50, 51–60, 51–100, 101–110, 101–150, 151–160, 151–200, 201–210, 201–250, 251–260, 251–300, 301–310, 301–350, 351–361, 351–400, 401–410, 401–439 of any of SEQ ID NOS:2, 4, 6, 8, 10 or 12.

Isolated nucleic acid molecules which encode polypeptides having 2,5-DKG permease activity, as well as the isolated oligonucleotides described above, will be subsequently referred as "2,5-DKG permease nucleic acid molecules."

The isolated 2,5-DKG permease nucleic acid molecules of the invention can be prepared by methods known in the art. The method chosen will depend on factors such as the type and size of nucleic acid molecule one intends to isolate; whether or not it encodes a biologically active polypeptide (e.g. a polypeptide having permease activity or immunogenicity); and the source of the nucleic acid molecule. Those skilled in the art can isolate or prepare 2,5-DKG permease nucleic acid molecules as genomic DNA or desired fragments therefrom; as full-length cDNA or desired fragments therefrom; or as full-length MRNA or desired fragments therefrom, from any microorganism of interest.

An exemplary method of preparing a 2,5-DKG permease nucleic acid molecule is by isolating a recombinant construct which encodes and expresses a polypeptide having 2,5-DKG permease activity. As described in the Example, one useful method is to provide a metabolic selection system where bacterial cell growth is made dependent on expression of a 2,5-DKG permease, introducing expressible DNA, such as a cDNA or genomic library, into the assay cells, selecting surviving cells under the selective conditions, and isolating the introduced DNA. Alternatively, a screening method can be designed, such that a cell will exhibit a detectable signal only when expressing a functional 2,5-DKG permease. An exemplary detectable signal is intracellular incorporation of a detectable label present on 2,5-DKG. Additionaly screening and selection strategies suitable for identifying nucleic acid molecules encoding metabolic enzymes are described, for example, in PCT publication WO 00/22170 and U.S. Pat. Nos. 5,958,672 and 5,783,431.

A further method for producing an isolated 2,5-DKG permease nucleic acid molecule involves amplification of the nucleic acid molecule using 2,5-DKG permease-specific primers and the polymerase chain reaction (PCR). Using PCR, a 2,5-DKG permease nucleic acid molecule having any desired boundaries can be amplified exponentially starting from as little as a single gene or mRNA copy, from any cell having a 2,5-DKG permease gene.

Given the high degree of identity among the six disclosed 2,5-DKG permeases, those skilled in the art can design suitable primers for isolating additional 2,5-DKG permease nucleic acid molecules. Such primers are preferably degenerate oligonucleotides that encode, or are complementary to, short consensus amino acid sequences present in two or more of the 2,5-DKG permeases disclosed herein, such as oligonucleotides that encode 10 or more contiguous amino acids present in at least two of SEQ ID NOS: 2, 6 and 10, or oligonucleotides that encode 10 or more contiguous amino acids present in at least two of SEQ ID NOS:4, 8 and 12. Such sequences can be determined from an alignment of amino acid sequences shown in FIG. 1. Exemplary amino acid sequences present in at least two of SEQ ID NOS:2, 6 and 10 are amino acids 19–31, 115–124, 146–156, and 339–348 of SEQ ID NO:2. Exemplary amino acid sequences present in at least two of SEQ ID NOS:4, 8 and 12 are amino acids 55–64, 60–69, 252–261, and 370–379 of SEQ ID NO:8.

Methods are well known in the art to determine or modify PCR reaction conditions when using degenerate primers to isolate a desired nucleic acid molecule. The amplified product can subsequently be sequenced, used as a hybridization probe, or used for 5' or 3' RACE to isolate flanking sequences, following procedures well known in the art and described, for example, in Ausubel et al., Current Protocols in Molecular Biology, John Wiley & Sons, New York (2000).

Given the high degree of sequence identity and structural relatedness among the six disclosed 2,5-DKG permeases, homologs from any other species can readily be identified by either hybridization or antibody screening. For example, an isolated 2,5-DKG permease nucleic acid molecule can be identified by screening a library, such as a genomic library, cDNA library or expression library, with a detectable nucleic acid molecule or antibody. Such libraries are commercially available from a variety of microorganisms, or can be produced from any available microorganism or environmental sample of interest using methods described, for example, in PCT publication WO 00/22170. The library clones identified as containing 2,5-DKG permease nucleic acid molecules can be isolated, subcloned and sequenced by routine methods.

Furthermore, 2,5-DKG permease nucleic acid molecules can be produced by direct synthetic methods. For example, a single stranded nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as oligonucleotide probes and primers, and also for producing nucleic acid molecules containing modified nucleotides or linkages.

The invention also provides an isolated polypeptide which has 2,5-DKG permease activity. Such isolated polypeptides, when expressed in their normal configuration at the cell membrane, are useful in applications in which enhanced uptake of 2,5-DKG is desirable, such as in bioproduction of 2-KLG. The isolated polypeptides of the invention can also be added to a culture medium, preferably in a membrane vesicle, to compete with membrane-bound permeases for 2,5-DKG, and thus to stop 2,5-DKG uptake. Thus, isolated polypeptides having 2,5-DKG permease activity can be used to regulate production of 2,5-DKG metabolites.

In one embodiment, an isolated polypeptide of the invention is not encoded by a nucleotide sequence completely contained within the nucleotide sequence designated SEQ ID NO:19 of WO 00/22170, which is the *K. oxytoca* yia operon. In another embodiment, an isolated polypeptide of the invention is not completely contained within the amino acid sequence herein designated SEQ ID NO:12.

An "isolated" polypeptide of the invention is altered by the hand of man from how it is found in its natural environment. For example, an isolated 2,5-DKG permease can be a molecule that is recombinantly expressed, such that it is present at a higher level in its native host, or is present in a different host. Alternatively, an "isolated" 2,5-DKG permease of the invention can be a substantially purified molecule. Substantially purified 2,5-DKG permeases can be prepared by methods known in the art. Specifically with respect to a polypeptide encoding the yiaX2 polypeptide designated SEQ ID NO:12, the term "isolated" is intended to mean that polypeptide is not present in association with the polypeptides expressed by other genes in the *K. oxytoca* yia operon, such as the genes, designated lyxK and orf1, described in WO 00/22170.

In one embodiment, an isolated polypeptide having. 2,5-DKG permease activity contains an amino acid sequence having at least 40% identity to an amino acid sequence selected from the group consisting of SEQ ID NOS:2, 4, 6, 8, 10 or 12. Preferably, the encoded polypeptide will have at least 45% identity to any of the recited SEQ ID NOS, such as at least 50%, 60%, 70%, 80% identity, including at least 90%, 95%, 98%, 99% or greater identity.

In another embodiment, the isolated polypeptide having 2,5-DKG permease activity contains at least 10 contiguous amino acids of any of SEQ ID NOS:2, 4, 6, 8, 10 or 12. Exemplary invention polypeptides contain an amino acid sequence of amino acids 1–10, 1–50, 51–60, 51–100, 101–110, 101–150, 151–160, 151–200, 201–210, 201–250, 251–260, 251–300, 301–310, 301–350, 351–361, 351–400, 401–410, 401–439 of any of SEQ ID NOS:2, 4, 6, 8, 10 or 12.

Also provided is an isolated immunogenic peptide having an amino acid sequence derived from a 2,5-DKG permease. Such isolated immunogenic peptides are useful, for example, in preparing and purifying 2,5-DKG antibodies. The term "immunogenic," as used herein, refers to a peptide that either is capable of inducing 2,5-DKG permease-specific antibodies, or capable of competing with 2,5-DKG permease-specific antibodies for binding to a 2,5-DKG permease. Peptides that are likely to be immunogenic can be predicted using methods and algorithms known in the art and described, for example, by Irnaten et al., *Protein Eng.* 11:949–955 (1998), and Savoie et al., *Pac. Symp. Biocomput.* 1999:182–189 (1999). The immunogenicity of the peptides of the invention can be confirmed by methods known in the art, such as by delayed-type hypersensitivity response assays in an animal sensitized to a 2,5-DKG permease, or by direct or competitive ELISA assays.

An isolated immunogenic peptide of the invention can contain at least 10 contiguous amino acids of a polypeptide selected from the group consisting of SEQ ID NOS:2, 4, 6, 8, 10 or 12, such as amino acids 1–10, 1–50, 51–60, 51–100, 101–110, 101–150, 151–160, 151–200, 201–210, 201–250, 251–260, 251–300, 301–310, 301–350, 351–361, 351–400, 401–410, 401–439 of any of SEQ ID NOS:2, 4, 6, 8, 10 or 12. Such a peptide can have at least 12, 15, 20, 25 or more contiguous amino acids of the reference sequence, including at least 30, 40, 50, 75, 100, 200, 300, 400 or more contiguous amino acids from the reference sequence, up to the full-length sequence.

For the production of antibodies that recognize 2,5-DKG permeases in their native configuration, such peptides will preferably contain at least part of an extracellular or intracellular domain from the permease. An extracellular or intracellular domain is generally characterized by containing at least one polar or positively or negatively charged residue, whereas a transmembrane domain is generally characterized as an uninterrupted stretch of about 20 contiguous hydrophobic residues. Commercially available computer topology programs can be used to determine whether a peptide is likely to correspond to an extracellular or intracellular domain or to a transmembrane region. Immunogenic peptides of the invention derived from a transmembrane region are useful to raise antibodies for use in applications such as immunoblotting, where the 2,5-DKG polypeptide need not be in its native configuration to be recognized.

The structural and functional characteristics and applications of 2,5-DKG permease polypeptides of the invention have been described above with respect to the encoding nucleic acid molecules, and are equally applicable in reference to the isolated polypeptides of the invention. Isolated polypeptides having 2,5-DKG permease activity, as well as the isolated immunogenic peptides of the invention, will subsequently be referred to as "2,5-DKG permeases."

Methods for recombinantly producing 2,5-DKG permeases have been described above with respect to nucleic acid molecules, vectors and cells of the invention. 2,5-DKG permeases can alternatively be prepared by biochemical procedures, by isolating membranes from bacteria that naturally express, or recombinantly express, 2,5-DKG permeases. The membranes can be further fractionated by size or affinity chromatography, electrophoresis, or immunoaffinity procedures, to achieve the desired degree of purity. Purification can be monitored by a variety of procedures, such as by immunoreactivity with 2,5-DKG permease antibodies, or by a functional assay.

Immunogenic peptides can be produced from purified or partially purified 2,5-DKG permease polypeptides, for example, by enzymatic or chemical cleavage of the full-length polypeptide. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990)).

Alternatively, 2,5-DKG permeases can be produced by chemical synthesis. If desired, such as to optimize their functional activity, stability or bioavailability, such chemically synthesized molecules can include D-stereoisomers, non-naturally occurring amino acids, and amino acid analogs and mimetics. Sawyer, *Peptide Based Drug Design*, ACS, Washington (1995) and Gross and Meienhofer, *The Peptides: Analysis. Synthesis, Biology*, Academic Press, Inc., New York (1983). For certain applications, such as for detecting the polypeptide, it can also be useful to incorporate one or more detectably labeled amino acids into a chemically synthesized permease, such as radiolabeled or fluorescently labeled amino acids.

An isolated 2,5-DKG permease of the invention can further be conjugated to carrier molecules, such as keyhole lympet hemocyanin, which can enhance recognition by the immune system of the isolated 2,5-DKG permease for production of antibodies. For certain applications, such as to increase the stability or bioactivity of the molecule, or to facilitate its identification, the 2,5-DKG permease can be chemically or enzymatically derivatized, such as by acylation, phosphorylation or glycosylation.

The invention also provides an antibody specific for a polypeptide having 2,5-DKG permease activity, such as an antibody specific for a polypeptide having the amino acid sequence of any of SEQ ID NOS:2, 4, 6, 8, 10 or 12. Also provided is an antibody specific for an isolated peptide that contains at least 10 contiguous amino acids of any of SEQ ID NOS:2, 4, 6, 8, 10 or 12, wherein the peptide is immunogenic. The antibodies of the invention can be used, for example, to detect or isolate 2,5-DKG permeases from expression libraries or cells.

The term "antibody," as used herein, is intended to include molecules having specific binding activity for a 2,5-DKG permease of at least about $1 \times 10^5$ $M^{-1}$, preferably at least $1 \times 10^7$ $M^{-1}$, more preferably at least $1 \times 10^9$ $M^{-1}$. The term "antibody" includes both polyclonal and monoclonal antibodies, as well as antigen binding fragments of such antibodies (e.g. Fab, F(ab')$_2$, Fd and Fv fragments and the like). In addition, the term "antibody" is intended to encompass non-naturally occurring antibodies, including, for example, single chain antibodies, chimeric antibodies, bifunctional antibodies, CDR-grafted antibodies and humanized antibodies, as well as antigen-binding fragments thereof.

Methods of preparing and isolating antibodies, including polyclonal and monoclonal antibodies, using peptide and polypeptide immunogens, are well known to those skilled in the art and are described, for example, in Harlow and Lane, *Antibodies: A Laboratory Manual*, Cold Spring Harbor Laboratory Press (1988). Non-naturally occurring antibodies can be constructed using solid phase peptide synthesis, can be produced recombinantly or can be obtained, for example, by screening combinatorial libraries consisting of variable heavy chains and variable light chains. Such methods are described, for example, in Huse et al. *Science* 246:1275–1281(1989); Winter and Harris, *Immunol. Today* 14:243–246 (1993); Ward et al., *Nature* 341:544–546 (1989); Hilyard et al., *Protein Engineering: A practical approach* (IRL Press 1992); and Borrabeck, *Antibody Engineering*, 2d ed. (Oxford University Press 1995).

The following example is intended to illustrate but not limit the present invention.

EXAMPLE

This example shows the isolation and characterization of nucleic acid molecules encoding six novel polypeptides having 2,5-DKG permease activity.

Identification of YiaX2 as a 2,5-DKG Permease

WO 002170 describes the identification and sequencing of an operon from *Klebsiella oxytoca*, designated the yia operon, which contains eight putative open reading frames. Because disruption of this operon abolished the ability of *K. oxytoca* to utilize ascorbic acid as the sole carbon source, the yia operon was predicted to be involved in the catabolism of ascorbic acid. The functions of the polypeptides encoded by the individual open reading frames in the yia operon were not described in WO 002170.

It was determined that *K. oxytoca* was able to grow on 2,5-DKG as a sole carbon source and, therefore, it was concluded that *K. oxytoca* expressed a 2,5-DKG permease. It was predicted that such a permease would share structural properties with known bacterial transporter proteins, such as multiple transmembrane segments. One of the uncharacterized open reading frames in the yia operon, designated yiaX2, encoded a transmembrane polypeptide with about 33% identity to a known tartrate transporter, and was thus considered a candidate 2,5-DKG permease.

In order to determine whether yiaX2 encoded a 2,5-DKG permease, this gene was deleted from the chromosome of the *K. oxytoca* strain designated M5a1. M5a1 has also been described in the literature as *K. pneumonia* (see, for example, Streicher et al., *Proc. Natl. Acad. Sci.* 68:1174–1177 (1971)). The yiaX2 deletion mutant was constructed by joining sequences immediately upstream and downstream of the yiaX2 gene in a three-way ligation with the pMAK705 integration vector (described in Hamilton et al., *J. Bacteriol.* 171:4617–4622 (1989)). A fragment of about 1 kb in the orf1 gene was amplified using oligonucleotides 5'-ACCCAAGCTTCACCAAAAGAGTGAAGAG-GAAG-3' (SEQ ID NO:17) and 5'-CGTATCTA-GAAAAATATTCTGGTGATGAAGGTGA-3 (SEQ ID NO:18), and digested with HindIII and XbaI. A fragment of a similar size in the lyxK gene was amplified with oligonucleotides 5'-AGACTCTAGATCCACATAAACGCACT-GCGTAAAC-3' (SEQ ID NO:19) and 5'-GAGGGGATC-CTGGCTTCGTGAACGATATACTGG-3' (SEQ ID NO:20), and digested with XbaI and BamHI. The two resulting fragments were ligated together between the HindIII and BamHI sites of the vector pMAK705. The resulting plasmid was transformed into *K. oxytoca* strain M5a1, and candidates in which the deletion construct had integrated by double crossover were obtained as described in Hamilton et al., supra (1989). The designation of the resulting *K. oxytoca* ΔyiaX2 strain is MGK002. The yiaX2-deficient phenotype was verified by by PCR analysis.

As described below, the *K. oxytoca* ΔyiaX2 [tkr idnO] strain was determined to grow very inefficiently on 2,5-DKG as the sole carbon source, and not to grow on 2-KLG. Confirmation that yiax2 encoded a polypeptide having 2,5-DKG and 2-KLG permease activities was obtained by determining that adding back the gene restored the ability of the *K. oxytoca* ΔyiaX2 [tkr idnO] to grow well on either 2,5-DKG or 2-KLG (see below).

Construction of *K. Oxytoca* ΔYiaX2 [tkr idnO]

In order to identify additional 2,5-DKG permeases, and preferably permeases selective for 2,5-DKG, a metabolic selection strategy was utilized. As described in WO 00/22170, metabolic selection is advantageous in allowing rapid identification of functional genes from uncharacterized and even unculturable microorganisms, without any prior sequence information.

A tester strain for the metabolic selection of nucleic acid molecules encoding 2,5-DKG permeases was prepared by engineering *K. oxytoca* ΔyiaX2 to express enzymes involved in the catabolism of 2,5-DKG to gluconic acid, which can be converted to carbon and energy. Enzymes capable of catabolizing 2,5-DKG to gluconic acid are encoded by the tkr and idnO genes of the tkr idnD idnO operon designated SEQ ID NO:13.

The tkr idnD idnO operon (SEQ ID NO:13) was subcloned into the high copy number vector pUC19 and the resulting clone, designated pDF33, was transformed into *K. oxytoca* ΔyiaX2. The resultingtester strain (designated MGK002[pDF33] or *K. oxytoca* ΔyiaX2 [tkr idnO]) thus expresses all polypeptides required for the utilization of 2,5-DKG as a sole carbon source, but is deficient in 2,5-DKG permease activity to transport extracellular 2,5-DKG into the cell. Therefore, a nucleic acid molecule that encodes a 2,5-DKG permease, upon expression in the tester strain, should confer the ability of the tester strain to grow on 2,5-DKG. The metabolic selection strategy is shown schematically in FIG. 3.

To validate the proposed metabolic selection strategy, as a positive control the yiaX2 gene was reintroduced into the tester strain to confirm that it conferred the ability to grow on 2,5-DKG and 2-KLG. The yiaX2 open reading frame (nucleotides 3777 to 5278 of SEQ ID NO:19 of WO 00/22170) was PCR-amplified using olignucleotides 5'-AATAGGATCCTTCATCACCAGAATATTTTA-3' (SEQ ID NO:21) and 5'-CATAGGTACCGGCTTTCAGAT-AGGTGCC-3' (SEQ ID NO:22) digested with BamH1 and Kpn1 and ligated into pCL1920 (Lerner et al., *Nucl. Acids. Res.* 18:4631 (1990); and see description below) previously digested with the same restriction enzymes. *K. oxytoca* ΔyiaX2 [tkr idnO], transformed with the resulting construct, was able to grow overnight at 30° C. on M9 minimal agar medium supplemented with either 2-KLG or 2,5-DKG (0.25%) and 0.1 mM IPTG. Therefore, *K. oxytoca* ΔyiaX2 [tkr idnO] was confirmed to be an appropriate tester strain to identify additional novel 2,5-DKG permeases, and to determine their selectivity.

Construction of Bacterial Genomic Libraries

The cloning vector used for constructing the above positive control and for preparing bacterial genomic libraries is plasmid pCL1920 (Lerner et al., supra, 1990), a low-copy number expression vector which carries a spectinomycin/streptomycin resistance determinant. Expression is driven by the lacPO promoter/operator region which is repressed by the lacI$^q$ gene product when provided by the host, and induced in the presence of 0.01 to 1 mM IPTG.

Genomic DNA from the following species and isolates was prepared according to the method outlined below: *Pantoea citrea* (ATCC 39140), *Klebsiella oxytoca* MGK002 (ΔyiaX2), *Pseudomonas aeruginosa*, and a mixture of 25 environmental isolates, obtained from 18 different soil and water samples, and able to grow on 2,5-DKG as the sole carbon source. *Klebsiella oxytoca* MGK002 (ΔyiaX2) was among the bacteria chosen because there was a slight amount of background growth observable in the tester strain on 2,5-DKG as the sole carbon source, and some 2,5-DKG permease activity in an uptake assay. However, the tester strain did not grow on 2-KLG, and exhibited no detectable 2-KLG uptake, suggesting the presence of a second 2,5-DKG permease with selectivity for 2,5-DKG in *K. oxytoca*.

Five milliliters of an overnight culture in LB (30° C.) were centrifuged for 5 min at 6,000 rpm. Pellets were washed with 1.5 ml Tris 10 mM, EDTA 1 mM pH 8.0 (TE), centrifuged again and resuspended in 0.4 ml TE. Lysozyme (5 mg/ml) and RNase (100 pg/ml) were added and cells were incubated for 10 min at 37° C. Sodium dodecylsulfate (SDS) was added to a final concentration of 1% and the tubes were gently shaken until lysis was complete. One hundred microliters of a 5N NaClO$_4$ stock solution were added to the lysate. The mixture was extracted once with one volume of phenol:chloroform (1:1) and once with one volume of chloroform. Chromosomal DNA was precipitated by adding 2 ml of cold (−20° C.) ethanol and gently coiling the precipitate around a curved Pasteur pipette. DNA was dried for 30 min at room temperature and resuspended in 50 to 100 μl of Tris 10 mM, EDTA 1 mM, NaCl 50 mM pH 8.0 to obtain a DNA concentration of 0.5 to 1 μg/μl. Genomic DNA preparations from each environmental isolate were mixed in equal ratios to prepare a single mixed library.

For each preparation, an aliquot of 10–15 μl of genomic DNA was subjected to Sau3A controlled digestion in order to obtain fragments ranging between 3 to 20 kb in size. Half that amount was ligated with the low-copy number expression vector pCL1920, which had previously been digested with BamHI and dephosphorylated. The resulting genomic libraries were transformed into E.coli DH10B electrocompetent cells (GIBCO-BRL) and briefly amplified overnight at 30° C. on LB-agar supplemented with 100 µg/ml spectinomycin. For each library, 30,000 to 120,000 clones were plated out and plasmid DNA was bulk-extracted using standard procedures. Insert size was randomly checked and the amplified libraries were stored in the form of plasmid DNA at −20° C. for further use in the tester strain.

Selection, Identification and Sequencing of Permease Genes

An aliquot of each genomic library was introduced by electroporation into the K. oxytoca ΔyiaX2 [tkr idnO] (MGK002[pDF33]) strain. The amount of DNA used in the transformation was adjusted in order to plate out $5\times10^5$ to $1\times10^6$ clones per library on the selective medium. Each selection round was plated on LB-agar containing 100 µg/ml spectinomycin, then replica-plated onto M9-agar plates containing 2.5% 2,5-DKG and 0.1 mM IPTG and adjusted to pH 4.5. The clones that grew on 2,5-DKG were transferred into K. oxytoca ΔyiaX2 (MGK002) devoid of plasmid pDF33, to verify that the tkr idnDO pathway was indeed required for growth of those clones on 2,5-DKG. A brief genetic characterization was performed to eliminate identical clones. Following preliminary 2,5-DKG/2-KLG uptake assays, 5 clones were retained for further analysis: 2 originated from the Pantoea citrea library, 1 from K. oxytoca and 2 from the mixed environmental library.

In all cases, DNA sequencing of the vector inserts revealed the presence of a nucleotide sequence (SEQ ID NOS:1, 3, 5, 7 and 9). encoding a polypeptide (SEQ ID NOS:2, 4, 6, 8 and 10) displaying homology with published transporters and with yiaX2 (SEQ ID NO:11, and its encoded polypeptide SEQ ID NO:12). Also present on these inserts were other orfs, and in most cases an endogenous promoter.

The insert containing both of the prmA and prmB orfs (SEQ ID NOS:7 and 9) was about 9 kb, and also contained an orf homologous to bacterial idnO, two orfs encoding transcriptional repressors, an orf of unknown function, and 3 orfs encoding homologs of E. coli polypeptides involved in nitrate utilization.

The insert containing the PE1 orf (SEQ ID NO:1) was about 3 kb, and also contained a putative dehydro-deoxygluconokinase gene closely related to the B. subtilis kdgK gene and a homolog of the E. coli ydcG gene.

The insert containing the PE6 orf (SEQ ID NO:3) was about 6.7 kb. The genomic environment of PE6 appeared similar to the yia operon of E. coli and K. oxytoca, as SEQ ID NO:4 was preceded by a yiaL homolog and a yiaK homolog was also present on the insert.

The insert containing the PK1 orf (SEQ ID NO:5) was about 5.5 kb. In contrast to the other inserts, this insert did not appear to contain an endogenous promoter, indicating that the PK1 orf was apparently transcribed from the vector's promoter. The PK1 orf was directly followed by a tkr homolog.

Nucleic acid molecules encoding each 2,5-DKG permease were reintroduced into K. oxytoca ΔyiaX2 [tkr idnO] and the resulting strains assayed for growth on 2,5-DKG and 2-KLG, and also assayed for uptake of radiolabeled 2,5-DKG and 2-KLG.

The uptake assays were performed by mixing radioactive 2-KLG or 2,5-DKG with IPTG-induced cells, removing aliquots at regular intervals, and measuring both the decrease in radioactivity in the supernatant and the appearance of radioactivity in the cells over time. The results of the growth assays and 2,5-DKG uptake assay are shown in Table 1, below.

TABLE 1

| Recombinantly expressed 2,5 DKG Permease | Cell Growth on 2,5-DKG | Cell Growth on 2-KLG | 2,5-DKG Uptake (g/l/h) |
|---|---|---|---|
| YiaX2 | + | ++ | 3.7 |
| PE1 | ++ | ++ | 4.2 |
| PE6 | ++ | ++ | 5.0 |
| prmA | ++ | ++ | 5.5 |
| prmB | +/− | ND | 0.9 |
| prmA and prmB | ++ | ND | 9.9 |
| PK1 | ++ | — | 4.2 |
| Control (K. oxytoca ΔyiaX2/ tkr/idn0) | bkgd | − | 1.0 |

Nucleic acid molecules encoding the different permeases were also subcloned into a variety of vectors, including the high copy number vector pSE380 (which contains a tac promoter), the medium copy number vector pACYC184 (which is promoterless), or the low copy number vector pCL1920, and introduced into a Pantoea strain suitable for bioproduction of 2-KLG from glucose (see U.S. Pat. No. 5,032,514). The resulting strains were assessed under biofermentation conditions to determine which combinations of nucleic acid molecules, promoters and vectors are optimal for enhancing 2-KLG production.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. A bacterial cell comprising a first isolated nucleic acid molecule encoding a polypeptide having 2,5-diketo-D-gluconic acid (2,5-DKG) permease activity and at least 95% sequence identity to SEQ ID NO:12 and second isolated nucleic acid molecule encoding a polypeptide having 5-keto reductase activity, said polypetide having at least 95% sequence identity to SEQ ID NO: 16, wherein said bacterial cell is deficient in endogenous 2,5-DKG permease activity.

2. A method of enhancing 2-keto-L-gluconic acid (2-KLG) production, comprising a) introducing an isolated nucleic acid molecule encoding a polypeptide having at least 96% sequence identity to SEQ ID NO: 12 into a bacterial cell which expresses an enzyme that catalyzes the conversion of 2,5-diketo-D-gluconic acid (2,5-DKG) to 2-KLG, b) allowing expression of the polypeptide encoded by said nucleic acid molecule and c) culturing the bacterial cell under suitable conditions to produce 2-KLG.

3. The method of claim 2, wherein said bacterial cell further expresses enzymes that catalyze the conversion of glucose to 2,5-DKG.

4. The method of claim 3, wherein said bacterial cell is deficient In endogenous 2-keto reductase activity.

5. The method of claim 2, wherein said bacterial cell is of the genus *Pantoea*.

6. The method of claim 2, further comprising converting said 2-KLG to ascorbic acid.

7. The bacterial cell of claim 1, which is an *E. coli* cell.

8. The method of claim 2, wherein the nucleic acid molecule has the sequence of SEQ ID NO: 11 or a sequence having at least 95% sequence identity thereto.

9. A method for increasing the transport of 2,5 diketo-D-gluconic acid (2,5 DKG) across a cell membrane into a bacterial host cell comprising a) introducing an isolated nucleic acid molecule into a bacterial host cell, wherein the nucleic acid molecule encodes a protein comprising at least 95% sequence identity to SEQ ID NO: 12 and said protein having 2,5 DKG permease activity, b) allowing expression of the protein and c) culturing the bacterial host cell under suitable conditions for the transport of 2,5-DKG into the bacterial host cell.

10. The method according to claim 9, wherein the bacterial host cell is an *E. coli, Pantoea* or *Klebsiella* host cell.

11. The method according to claim 9, wherein the nucleic acid molecule has the sequence of SEQ ID NO: 11 or a sequence having at least 95% sequence identity thereto.

12. The method according to claim 2, wherein said polypeptide has the sequence of SEQ ID NO: 12.

13. The method according to claim 2, wherein the bacterial host cell is an *E coli, Pantoea* or *Klebsiella* host cell.

14. The method according to claim 9, wherein said polypeptide has the sequence of SEQ ID NO: 12.

15. The method according to claim 10, wherein the bacterial host cell is a *Klebsiella* cell.

16. The method according to claim 10, wherein the bacterial host cell is an *E. coli* cell.

17. The method according to claim 10, wherein the bacterial host cell is a *Pantoea* cell.

18. The method according to claim 10, wherein the bacterial host cell is deficient in endogenous 2,5 DKG permease activity.

19. The method according to claim 10, wherein the bacterial host cell further comprises a nucleic acid molecule encoding a polypeptide having 2-keto reductase activity and at least 95% sequence identity to SEQ ID NO: 14.

20. The method according to claim 10, wherein the bacterial host cell further comprises an isolated nucleic acid molecule having 5-keto reductase activity and at least 95% sequence identity to SEQ ID NO: 16.

21. The method according to claim 10, wherein the bacterial host cell expresses an enzyme that catalyzes the conversion of 2,5-DKG to 2-keto-L-gluconic acid (2-KLG).

22. The method according to claim 10, wherein the nucleic acid molecule encoding the protein having 2,5-DKG permease activity is operably linked to a lac promoter.

23. The method of claim 2, wherein the nucleic acid molecule encodes a polypeptide having at least 98% sequence identity to SEQ ID NO: 12.

24. The method of claim 23, wherein the nucleic acid molecule encodes a polypeptide having at least 99% sequence identity to SEQ ID NO: 12.

25. The bacterial cell of claim 1, wherein said cell is from the genus *Pantoea*.

26. The bacterial cell of claim 1, wherein the first nucleic acid molecule encodes a polypeptide having at least 98% sequence identity to SEQ ID NO:12 and the second nucleic acid encodes a polypeptide having at least 95% sequence identity to SEQ ID NO:16.

27. The method of claim 9, wherein the nucleic acid molecule encodes a polypeptide having at least 98% sequence Identity to SEQ ID NO: 12.

28. The method of claim 27, wherein the nucleic acid molecule encodes a polypeptide having at least 99% sequence identity to SEQ ID NO: 12.

* * * * *